US012698496B2

(12) United States Patent
Chen et al.

(10) Patent No.: US 12,698,496 B2
(45) Date of Patent: Aug. 4, 2026

(54) T4 RNA LIGASE 2 MUTANTS AND PREPARATION METHOD AND USE THEREOF

(71) Applicant: HONGENE BIOTECH PTE. LTD., Singapore (SG)

(72) Inventors: Zhipeng Chen, Singapore (SG); Minzhi Wei, Singapore (SG)

(73) Assignee: HONGENE BIOTECH PTE. LTD., Singapore (SG)

( * ) Notice: Subject to any disclaimer, the term of this patent is extended or adjusted under 35 U.S.C. 154(b) by 0 days.

(21) Appl. No.: 19/251,886

(22) Filed: Jun. 27, 2025

(65) Prior Publication Data

US 2026/0209741 A1    Jul. 23, 2026

(30) Foreign Application Priority Data

Jan. 23, 2025    (CN) ......................... 202510110925.X

(51) Int. Cl.
*C12N 9/00*        (2006.01)
*C12P 19/30*        (2006.01)

(52) U.S. Cl.
CPC ................ *C12N 9/93* (2013.01); *C12P 19/30* (2013.01); *C12Y 605/01003* (2013.01)

(58) Field of Classification Search
CPC .... C12N 9/93; C12P 19/30; C12Y 605/01003
See application file for complete search history.

(56) References Cited

FOREIGN PATENT DOCUMENTS

CN        117106782 A        11/2023

OTHER PUBLICATIONS

UniProt Accession No. A0A6B9Y014, created Jun. 17, 2020, Title: RNA ligase 2. (Year: 2020).*

Whisstock et al. Quaterly Reviews of Biophysics, 2003, "Prediction of protein function from protein sequence and structure", 36(3):307-340. (Year: 2003).*

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*

Kisselev L., Polypeptide release factors in prokaryotes and eukaryotes: same function, different structure. Structure, 2002, vol. 10: 8-9. (Year: 2002).*

OA1 of priority document of CN202510110925.X, China National Intellectual Property Administration, issued on Sep. 4, 2025, pp. 1-6.

PDB: 2HVR_A, Chain A, T4 RNA ligase 2, National Center for Biotechnology Information (NCBI), 2023, pp. 1-2, retrieved from: https://www.ncbi.nlm.nih.gov/protein/2HVRA/.

NCBI Reference Sequence: WP_371335562.1, Multispecies: RNA ligase, Rnl2 family [Bacteria], National Center for Biotechnology Information (NCBI), 2025, pp. 1-2, retrieved from: https://www.ncbi.nlm.nih.gov/protein/WP371335562.1.

* cited by examiner

*Primary Examiner* — Iqbal H Chowdhury
(74) *Attorney, Agent, or Firm* — Bayramoglu Law Offices LLC

(57)        ABSTRACT

Provided are T4 RNA ligase 2 mutants and preparation method and use thereof, relating to the field of biology and enzyme engineering. The T4 ligase 2 mutants have mutation at least one site of positions 62, 103, 166, 168, 193, 217, 260, 297, 298, 303, 306, 311, 313 and 318 of sequence of the wild-type T4 RNA ligase 2. Compared with the wild type, the mutants have remarkably improved thermal stability, and can maintain relatively high ligase activity at higher temperatures such as 45° C., and 50° C. In addition to ligating natural nucleic acid sequences, the mutants further can ligate non-natural nucleic acids with modification at high temperatures. The mutants can synthesize ribonucleic acids at elevated temperatures, so as to effectively reduce the production of byproducts caused by base mismatching, thus improving the efficiency of RNA synthesis, and facilitating large-scale production of high-quality RNAs.

6 Claims, 7 Drawing Sheets

Specification includes a Sequence Listing.

SS: 5' fU-fA-mG-fA-mC-fC-mC-mG-mA-mC-fA-mU-fG-mU-fU-fC-mC-fG 3'  (SEQ ID NO. 29)

AS: 3' mA-fU-mC-fU-fG-fG-mG-fC-mU-fG-fU-mA-fC-mA-mA-fG-mG-fC 5'  (SEQ ID NO. 30)

SS: 5' Pho-A-C-G-C-A-U-G-A-A-C-U-G-C-U-A-C-U-U-A-U-C-A 3'  (SEQ ID NO. 34)

AS: 3' U-G-C-G-U-A-C-U-U-G-A-C-G-A-U-G-A-A-U-A-G-U 5'  (SEQ ID NO. 35)

SS: 5' VP-mA-fC-mG-fC-mA-dT-fG-mA msA-fC-mU-msG-fC-mU-fsA-mC-fU-mU-mA-fU-msC-fA 3' (SEQ ID NO. 36)

AS: 3' mU-mG-mC-fG-mU-fA-mC-fU-mU-fG-msA mC-fG-mA-dU-mG-fA-mA-fU-mA-fG-mU 5'  (SEQ ID NO. 37)

Figure 10:
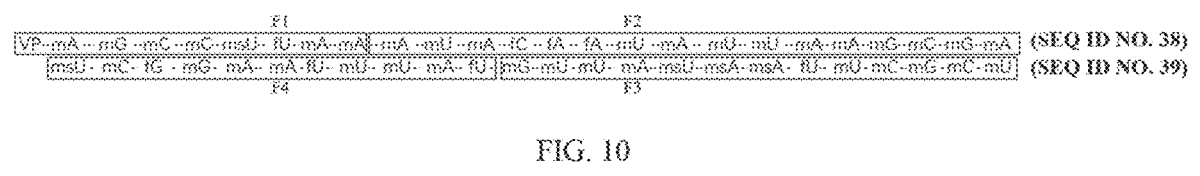

F1                           F2

VP-mA--mG--mC--mC-msU--fU-mA-mA--mA--mU--mA--fC--fA--fA--mU--mA--mU--mU--mA-mA-mG-mC-mG-mA   (SEQ ID NO. 38)

msU--mC--fG--mG--mA--mA-fU--mU--mU--mA--fU-|mG--mU--mU--mA--msU--msA--msA--fU--mU--mC--mG--mC--mU|   (SEQ ID NO. 39)

SEQUENCE LISTING

```
Sequence total quantity: 39
SEQ ID NO: 1              moltype = AA   length = 334
FEATURE                  Location/Qualifiers
source                   1..334
                         mol_type = protein
                         organism = synthetic construct
SEQUENCE: 1
MFKKYSSLEN HYNSKFIEKL YSLGLTGGEW VAREKIHGTN FSLIIERDKV TCAKRTGPIL  60
PAEDFFGYEI ILKNYADSIK AVQDIMETSA VVSYQVFGEF AGPGIQKNVD YCDKDFYVFD  120
IIVTTESGDV TYVDDYMMES FCNTFKFKMA PLLGRGKFEE LIKLPNDLDS VVQDYNFTVD  180
HAGLVDANKC VWNAEAKGEV FTAEGYVLKP CYPSWLRNGN RVAIKCKNSK FSEKKKSDKP  240
IKAKVELSEA DNKLVGILAC YVTLNRVNNV ISKIGEIGPK DFGKVMGLTV QDILEETSRE  300
GITLTQADNP SLIKKELVKM VQDVLRPAWI ELVS                            334

SEQ ID NO: 2              moltype = AA   length = 334
FEATURE                  Location/Qualifiers
source                   1..334
                         mol_type = protein
                         organism = synthetic construct
SEQUENCE: 2
MFKKYSSLEN HYNSKFIEKL YSLGLTGGEW VAREKIHGTN FSLIIERDKV TCAKRTGPIL  60
PAEDFFGYEI ILKNYADSIK AVQDIMETSA VVSYQVFGEF AGPGIQKNVD YGDKDFYVFD  120
IIVTTESGDV TYVDDYMMES FCNTFKFKMA PLLGRGKFEE LIKLPNDLDS VVQDYNFTVD  180
HAGLVDANKC VWNAEAKGEV FTAEGYVLKP CYPSWLRNGN RVAIKCKNSK FSEKKKSDKP  240
IKAKVELSEA DNKLVGILAC YVTLNRVNNV ISKIGEIGPK DFGKVMGLTV QDILEETSRE  300
GITLTQADNP SLIKKELVKM VQDVLRPAWI ELVS                            334

SEQ ID NO: 3              moltype = DNA   length = 1005
FEATURE                  Location/Qualifiers
source                   1..1005
```

```
                       mol_type = other DNA
                       organism = synthetic construct
SEQUENCE: 3
atgtttaaga agtactcctc ccttgagaac cattataaca gcaagttcat tgagaagctg    60
tattctttgg gtttgacggg cggtgaatgg gtcgctcgtg agaaaatcca cggcaccaat   120
ttttccctga tcattgagcg cgataaagta acgtgcgcga agcgcaccgg tccgattctg   180
ccggcggagg atttcttcgg ctatgaaatc attctcaaaa actatgccga ctccattaag   240
gcggttcaag atatcatgga aacctctgct gtggttagct accaggtttt cggcgagttt   300
gcgggaccag gtattcaaaa aaacgtggac tattgcgaca aggacttcta cgtgtttgac   360
atcatcgtta cgaccgaaag cggtgatgtt acctatgttg acgactacat gatggagagc   420
ttctgcaaca cctttaagtt caagatggca ccactgttgg gccgtggtaa atttgaagag   480
ttgatcaagc tgccgaacga tctggattcg gtcgtgcagg attacaactt caccgtcgac   540
catgcgggcc tagttgacgc taataaatgt gtttggaatg cagaggcgaa gggcgaggtg   600
ttcaccgcag agggctacgt tctgaaaccg tgctacccga gctggctgcg taatggtaat   660
cgtgttgcga ttaagtgcaa gaacagcaaa ttttcggaaa aaaagaaaag cgataaaccg   720
attaaggcca aggtggaact gagcgaggcg gataacaagt tagtgggtat cttggcatgt   780
tacgttactt tgaatcgcgt taataacgtc atcagcaaaa tcggtgaaat tggtccgaaa   840
gactttggca aagtgatggg tctgacggtg caagacatcc tggaggaaac ttcaagagg    900
ggcatcaccc tgacccaggc tgacaacccg tctctgatta aaaaagaact ggtgaaaatg   960
gtgcaggatg tgttacgtcc ggcctggatt gaactggtga gctaa                  1005

SEQ ID NO: 4            moltype = DNA   length = 1005
FEATURE                Location/Qualifiers
source                 1..1005
                       mol_type = other DNA
                       organism = synthetic construct
SEQUENCE: 4
atgtttaaga agtactcctc ccttgagaac cattataaca gcaagttcat tgagaagctg    60
tattctttgg gtttgacggg cggtgaatgg gtcgctcgtg agaaaatcca cggcaccaat   120
ttttccctga tcattgagcg cgataaagta acgtgcgcga agcgcaccgg tccgattctg   180
ccggcggagg atttcttcgg ctatgaaatc attctcaaaa actatgccga ctccattaag   240
gcggttcaag atatcatgga aacctctgct gtggttagct accaggtttt cggcgagttt   300
gcgggaccag gtattcaaaa aaacgtggac tatggtgaca aggacttcta cgtgtttgac   360
atcatcgtta cgaccgaaag cggtgatgtt acctatgttg acgactacat gatggagagc   420
ttctgcaaca cctttaagtt caagatggca ccactgttgg gccgtggtaa atttgaagag   480
ttgatcaagc tgccgaacga tctggattcg gtcgtgcagg attacaactt caccgtcgac   540
catgcgggcc tagttgacgc taataaatgt gtttggaatg cagaggcgaa gggcgaggtg   600
ttcaccgcag agggctacgt tctgaaaccg tgctacccga gctggctgcg taatggtaat   660
cgtgttgcga ttaagtgcaa gaacagcaaa ttttcggaaa aaaagaaaag cgataaaccg   720
attaaggcca aggtggaact gagcgaggcg gataacaagt tagtgggtat cttggcatgt   780
tacgttactt tgaatcgcgt taataacgtc atcagcaaaa tcggtgaaat tggtccgaaa   840
gactttggca aagtgatggg tctgacggtg caagacatcc tggaggaaac ttcaagagag   900
ggcatcaccc tgacccaggc tgacaacccg tctctgatta aaaaagaact ggtgaaaatg   960
gtgcaggatg tgttacgtcc ggcctggatt gaactggtga gctaa                  1005

SEQ ID NO: 5            moltype = DNA   length = 59
FEATURE                Location/Qualifiers
misc_feature           1
                       note = RNA
misc_feature           2
                       note = DNA
misc_feature           3..59
                       note = RNA
source                 1..59
                       mol_type = other DNA
                       organism = synthetic construct
SEQUENCE: 5
ctcgatagtc tcagctgatt tttcagctga gactatcgag agtacagtca gtcagtcaa    59

SEQ ID NO: 6            moltype = DNA   length = 19
FEATURE                Location/Qualifiers
misc_feature           1..15
                       note = RNA
misc_feature           16
                       note = DNA
misc_feature           17..19
                       note = RNA
source                 1..19
                       mol_type = other DNA
                       organism = synthetic construct
SEQUENCE: 6
ttgactgact gactgtact                                                 19

SEQ ID NO: 7            moltype = RNA   length = 11
FEATURE                Location/Qualifiers
source                 1..11
                       mol_type = other RNA
                       organism = synthetic construct
SEQUENCE: 7
```

-continued

```
tagacccgac a                                                            11

SEQ ID NO: 8           moltype =   length =
SEQUENCE: 8
000

SEQ ID NO: 9           moltype = RNA   length = 11
FEATURE                Location/Qualifiers
source                 1..11
                       mol_type = other RNA
                       organism = synthetic construct
SEQUENCE: 9
cggaacatgt c                                                            11

SEQ ID NO: 10          moltype =   length =
SEQUENCE: 10
000

SEQ ID NO: 11          moltype = RNA   length = 15
FEATURE                Location/Qualifiers
source                 1..15
                       mol_type = other RNA
                       organism = synthetic construct
SEQUENCE: 11
gaacttggac agaat                                                        15

SEQ ID NO: 12          moltype =   length =
SEQUENCE: 12
000

SEQ ID NO: 13          moltype =   length =
SEQUENCE: 13
000

SEQ ID NO: 14          moltype =   length =
SEQUENCE: 14
000

SEQ ID NO: 15          moltype =   length =
SEQUENCE: 15
000

SEQ ID NO: 16          moltype =   length =
SEQUENCE: 16
000

SEQ ID NO: 17          moltype = RNA   length = 14
FEATURE                Location/Qualifiers
source                 1..14
                       mol_type = other RNA
                       organism = synthetic construct
SEQUENCE: 17
actgctactt atca                                                         14

SEQ ID NO: 18          moltype = RNA   length = 11
FEATURE                Location/Qualifiers
source                 1..11
                       mol_type = other RNA
                       organism = synthetic construct
SEQUENCE: 18
tgataagtag c                                                            11

SEQ ID NO: 19          moltype = RNA   length = 11
FEATURE                Location/Qualifiers
source                 1..11
                       mol_type = other RNA
                       organism = synthetic construct
SEQUENCE: 19
agttcatgcg t                                                            11

SEQ ID NO: 20          moltype =   length =
SEQUENCE: 20
000

SEQ ID NO: 21          moltype = RNA   length = 14
FEATURE                Location/Qualifiers
source                 1..14
                       mol_type = other RNA
                       organism = synthetic construct
```

-continued

```
SEQUENCE: 21
actgctactt atca                                                              14

SEQ ID NO: 22        moltype = RNA   length = 11
FEATURE              Location/Qualifiers
source               1..11
                     mol_type = other RNA
                     organism = synthetic construct
SEQUENCE: 22
tgataagtag c                                                                 11

SEQ ID NO: 23        moltype = RNA   length = 11
FEATURE              Location/Qualifiers
source               1..11
                     mol_type = other RNA
                     organism = synthetic construct
SEQUENCE: 23
agttcatgcg t                                                                 11

SEQ ID NO: 24        moltype =    length =
SEQUENCE: 24
000

SEQ ID NO: 25        moltype = RNA   length = 16
FEATURE              Location/Qualifiers
source               1..16
                     mol_type = other RNA
                     organism = synthetic construct
SEQUENCE: 25
atacaatatt aagcga                                                            16

SEQ ID NO: 26        moltype = RNA   length = 13
FEATURE              Location/Qualifiers
source               1..13
                     mol_type = other RNA
                     organism = synthetic construct
SEQUENCE: 26
tcgcttaata ttg                                                               13

SEQ ID NO: 27        moltype = RNA   length = 11
FEATURE              Location/Qualifiers
source               1..11
                     mol_type = other RNA
                     organism = synthetic construct
SEQUENCE: 27
tatttaaggc t                                                                 11

SEQ ID NO: 28        moltype = RNA   length = 78
FEATURE              Location/Qualifiers
source               1..78
                     mol_type = other RNA
                     organism = synthetic construct
modified_base        16
                     mod_base = OTHER
                     note = thymine
modified_base        21
                     mod_base = OTHER
                     note = thymine
SEQUENCE: 28
ttgactgact gactgtactc tcgatagtct cagctgattt ttcagctgag actatcgaga   60
gtacagtcag tcagtcaa                                                  78

SEQ ID NO: 29        moltype = RNA   length = 18
FEATURE              Location/Qualifiers
source               1..18
                     mol_type = other RNA
                     organism = synthetic construct
SEQUENCE: 29
tagacccgac atgttccg                                                          18

SEQ ID NO: 30        moltype = RNA   length = 17
FEATURE              Location/Qualifiers
source               1..17
                     mol_type = other RNA
                     organism = synthetic construct
SEQUENCE: 30
cggaacatgt cgggtct                                                           17

SEQ ID NO: 31        moltype = RNA   length = 15
```

-continued

```
FEATURE              Location/Qualifiers
source               1..15
                     mol_type = other RNA
                     organism = synthetic construct
SEQUENCE: 31
ccaatgtcca agttc                                              15

SEQ ID NO: 32        moltype = RNA   length = 15
FEATURE              Location/Qualifiers
source               1..15
                     mol_type = other RNA
                     organism = synthetic construct
SEQUENCE: 32
ccaaagtcca agttc                                              15

SEQ ID NO: 33        moltype = RNA   length = 15
FEATURE              Location/Qualifiers
source               1..15
                     mol_type = other RNA
                     organism = synthetic construct
SEQUENCE: 33
ccaaaatcca agttc                                              15

SEQ ID NO: 34        moltype = RNA   length = 22
FEATURE              Location/Qualifiers
source               1..22
                     mol_type = other RNA
                     organism = synthetic construct
SEQUENCE: 34
acgcatgaac tgctacttat ca                                      22

SEQ ID NO: 35        moltype = RNA   length = 22
FEATURE              Location/Qualifiers
source               1..22
                     mol_type = other RNA
                     organism = synthetic construct
SEQUENCE: 35
tgataagtag cagttcatgc gt                                      22

SEQ ID NO: 36        moltype = RNA   length = 22
FEATURE              Location/Qualifiers
source               1..22
                     mol_type = other RNA
                     organism = synthetic construct
SEQUENCE: 36
acgcatgaac tgctacttat ca                                      22

SEQ ID NO: 37        moltype = RNA   length = 22
FEATURE              Location/Qualifiers
source               1..22
                     mol_type = other RNA
                     organism = synthetic construct
SEQUENCE: 37
tgataagtag cagttcatgc gt                                      22

SEQ ID NO: 38        moltype = RNA   length = 24
FEATURE              Location/Qualifiers
source               1..24
                     mol_type = other RNA
                     organism = synthetic construct
SEQUENCE: 38
agccttaaat acaatattaa gcga                                    24

SEQ ID NO: 39        moltype = RNA   length = 24
FEATURE              Location/Qualifiers
source               1..24
                     mol_type = other RNA
                     organism = synthetic construct
SEQUENCE: 39
tcgcttaata ttgtatttaa ggct                                    24
```

T4 RNA LIGASE 2 MUTANTS AND PREPARATION METHOD AND USE THEREOF

CROSS-REFERENCE TO RELATED APPLICATION

The present disclosure claims the priority to the Chinese patent application with the filing No. 202510110925.X filed with the Chinese Patent Office on Jan. 23, 2025, the contents of which are incorporated herein by reference in entirety.

TECHNICAL FIELD

The present disclosure relates to the field of biology and enzyme engineering, and specifically to T4 RNA ligase 2 mutants and preparation method and use thereof.

BACKGROUND ART

RNA-based drugs are a novel type of drugs that have attracted significant attention in recent years, and have been widely explored in the field for treatment of various diseases, such as tumors, rare diseases, gastrointestinal diseases, cardiovascular diseases and metabolic disorders. Compared with the conventional research and development of small molecular drugs and protein drugs, RNA-based drugs have many advantages, including rapid research, development and synthesis, high target specificity, and highly customization, among others. RNA-based drugs substantially can be divided into four categories: RNA aptamers, antisense nucleotide (antisense oligonucleotide, ASO) drugs, RNA interference (miRNA and siRNA) drugs and messenger RNA (mRNA) drugs. In addition to serving as RNA-based drugs, RNA also plays an important role in gene editing techniques. In the widely used CRISPR-Cas gene editing technique, single guide RNA (gRNA) can form a complex with DNA endonuclease Cas, and locate a genomic loci to be edited by complementary pairing, thereby initiating a Cas-mediated gene editing process. With the rise of RNA products in the pharmaceutical field, the demand for RNA synthesis has been increasing year by year.

At present, for chemical synthesis of RNA, ribonucleotide residues are generally serially linked and extended in sequence, with 1 nucleotide each time, to prepare nucleotide strands of interest. Since the efficiency of chemical synthesis reaction of ribonucleotide strands cannot reach 100%, thus product purity and yield of target product of synthesized ribonucleotide strands of interest both decrease with the increase of length of the nucleotide strands of interest, resulting in that a synthesized product contains a certain amount of non-target nucleotide strands whose length does not accord with that of the nucleotide strands of interest.

For nucleotide strands chemically synthesized with a length less than or equal to 20 nt, a proportion of nucleotide strands of interest finally in a synthesized product can be increased by a purification process (for example, ion exchange column or reverse phase column). However, since the length of a part of the non-target nucleotide strands is relatively close to the length of the nucleotide strands of interest (for example, the length of the non-target nucleotide strands only differs from the length of the nucleotide strands of interest by 1 nt or 2 nt), these non-target nucleotide strands are quite close to the nucleotide strands of interest in property, so that these non-target nucleotide strands cannot be effectively separated or removed from the synthesized product. For nucleotide strands greater than 20 nt in length, particularly nucleotide strands greater than 50 nt in length, and even nucleotide strands greater than 100 nt in length, after chemical synthesis thereof, more non-target nucleotide strands cannot be effectively separated or removed from the synthesized product.

The presence of the non-target nucleotide strands in the synthesized product often affects function, activity, etc. of target drugs, and particularly for cases where the nucleotide strands of interest are antisense nucleotide drugs, SiRNA drugs, nucleic acid aptamer drugs, sgRNA drugs, etc., the presence of the non-target nucleotide strands seriously affects the nucleotide strands of interest in exerting efficacy thereof.

Presently, oligonucleotide fragments can be ligated by a ligase so as to obtain a nucleotide strand of interest, thereby improving the yield of the nucleotide strands of interest and reducing impurities. With regard to the method for obtaining nucleotide strands of interest by ligating oligonucleotide fragments by a ligase, the ligase which catalyzes a double-stranded RNA ligation reaction is crucial. The most commonly used and most thoroughly studied RNA double-stranded ligase is T4 RNA ligase 2.

T4 RNA ligase 2 (T4 Rnl2) is an RNA ligase isolated from T4 bacteriophage. T4 Rnl2 is an ATP-dependent 5'-3' RNA ligase (EC6.5.1.3) capable of efficiently catalyzing ligation reaction of nick in double-stranded RNA and RNA nick immobilized by DNA splint. T4 Rnl2 catalyzes ligation reaction of a nucleic acid substrate through three-step reaction: firstly, Lys 35 on T4 Rnl2 reacts with ATP to form a ligase-AMP intermediate, releasing pyrophosphate; subsequently, AMP is transferred to 5'-PO$_4$ (donor) at the nick, forming an RNA-adenylate intermediate (AppRNA); and finally, the ligase drives 3'-OH (acceptor) at the RNA nick to attack AppRNA, forming a phosphodiester bond, sealing the nick, and releasing AMP. As the most commonly used RNA ligase in a small RNA synthesis process. T4 Rnl2 offers advantages such as high ligation rate, absence of sequence bias, and compatibility with various modified nucleosides. However, during practical production, especially during multi-fragment ligation, base mismatching in the ligation substrate often leads to byproducts. The presence of these byproducts reduces the yield of the target product and increases the difficulty of purification of the target product.

In view of this, the present disclosure is specifically proposed.

SUMMARY

The present disclosure aims at providing T4 RNA ligase 2 mutants and preparation method and use thereof.

The present disclosure is implemented as follows.

In the first aspect, embodiments of the present disclosure provide a T4 RNA ligase 2 mutant, where compared with wild-type T4 RNA ligase 2, the T4 ligase 2 mutant has mutation at any one or more sites of positions 62, 103, 166, 168, 193, 217, 260, 297, 298, 303, 306, 311, 313 and 318 of an amino acid sequence of the wild-type T4 RNA ligase 2.

In the second aspect, embodiments of the present disclosure provide an isolated nucleic acid, encoding the T4 RNA ligase 2 mutant according to the preceding embodiments.

In the third aspect, embodiments of the present disclosure provide a vector, comprising the isolated nucleic acid according to the preceding embodiments.

In the fourth aspect, embodiments of the present disclosure provide a host cell, comprising the vector according to the preceding embodiments.

In the fifth aspect, embodiments of the present disclosure provide a preparation method for the T4 RNA ligase 2 mutant according to the preceding embodiments, comprising: culturing the host cell according to the preceding embodiments.

In the sixth aspect, embodiments of the present disclosure provide use of the T4 RNA ligase 2 mutant according to the preceding embodiments in synthesis of nucleotide strands or in preparation of a product for synthesis of nucleotide strands of interest.

The present disclosure has the following beneficial effects.

(1) Through rational design of T4 RNA ligase 2, a group of T4 RNA ligase 2 mutants are obtained. The thermal stability of the mutants obtained is remarkable improved and they are able to maintain high ligase activity. Compared with the wild-type T4 RNA ligase 2, the thermostable mutants still have high ligase activity at high temperatures such as 45° C. and 50° C.;

(2) In addition to ligating natural RNA sequences, the T4 RNA ligase 2 mutants provided in embodiments of the present disclosure further can ligate nucleic acid substrates with modification.

(3) The T4 RNA ligase 2 mutants provided in embodiments of the present disclosure can ligate nicked double-stranded nucleic acid molecules at high temperatures, so as to synthesize RNA duplexes and/or RNA/DNA hybrid duplexes, thus reducing the production of byproducts caused by base mismatching, improving the efficiency of synthesis of nucleotide strands, and facilitating large-scale production of high-quality nucleic acid-based drugs.

BRIEF DESCRIPTION OF DRAWINGS

In order to more clearly illustrate technical solutions of embodiments of the present disclosure, drawings which need to be used in the embodiments will be briefly introduced below. It should be understood that the drawings merely show some embodiments of the present disclosure, and thus should not be considered as limitation to the scope, and those ordinarily skilled in the art still could obtain other relevant drawings according to the drawings, without using any inventive efforts.

Figure 5:
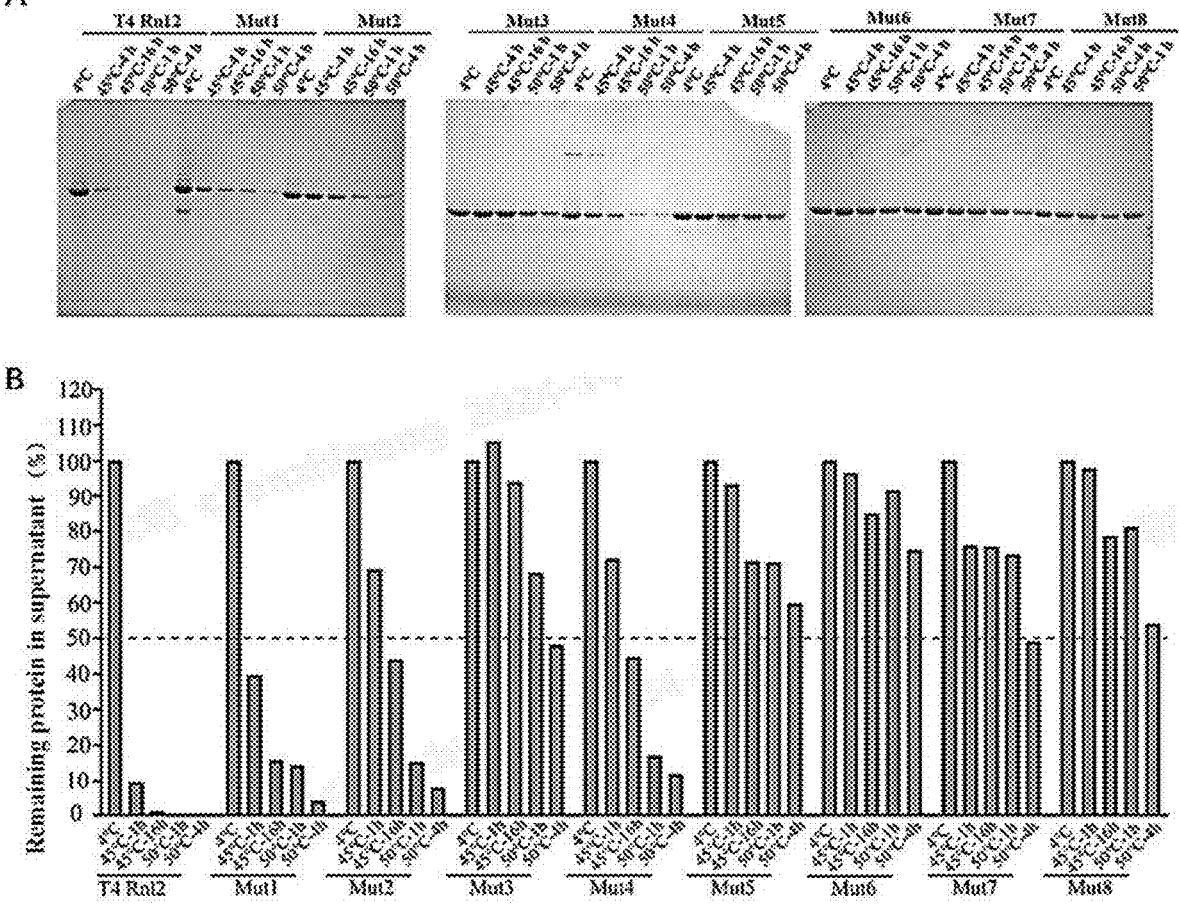
Figures 6, 7, 8, 9:
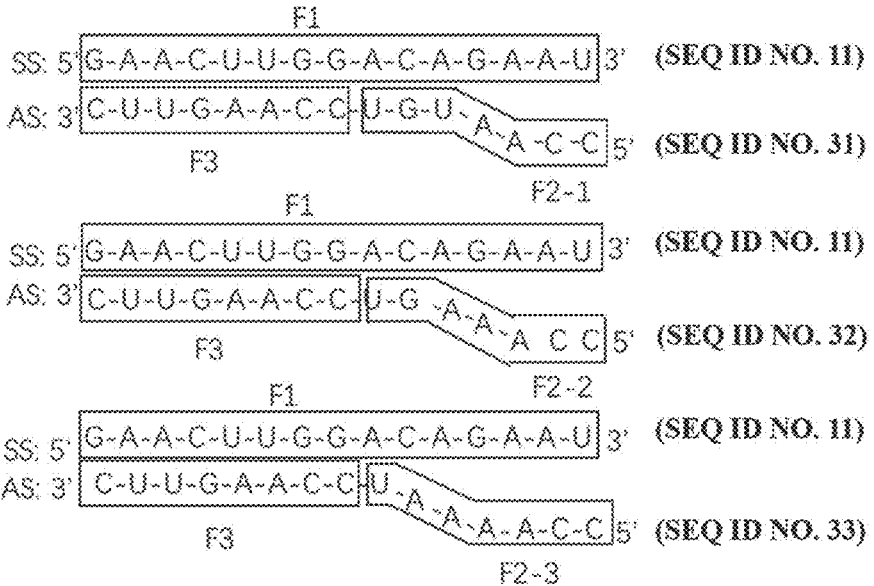

A in FIG. 5 shows SDS-PAGE results of protein in supernatant after T4 Rnl2 and mutants thereof are heated at 45° C. for 1 h and 16 h, or heated at 50° C. for 1 h and 4 h, respectively, and subjected to high-speed centrifugation; and B shows ratios of protein in supernatant after treatment at different temperatures upon grayscale integration of various electrophoresis bands in A to those after incubation at 4° C.;

FIG. 6 shows oligonucleotides and ligation products thereof used in Example 6;

FIG. 7 shows ribonucleotide fragments and ligation products thereof used in Example 7;

FIG. 8 shows oligonucleotides and ligation products thereof used in Example 8;

FIG. 9 shows oligonucleotides and ligation products thereof used in Example 9; and FIG. 10 shows oligonucleotides and ligation products thereof used in Example 10.

DETAILED DESCRIPTION OF EMBODIMENTS

In the description below, many professional terms are used. In order to have a clearer and consistent understanding of the description and claims, including specified scopes of these terms, the following definitions are provided.

Oligonucleotide: it generally refers to a linear polynucleotide fragment composed of 2-10 nucleotide residues linked by phosphodiester bonds. However, it should be noted that the number of nucleotides of an oligonucleotide is not strictly specified, and in some literature, polynucleotide molecules containing 30 or more, up to 200, 300, 400, or 500 nucleotide residues may also be referred to as oligonucleotides.

Natural ribonucleotide: it consists of one molecule of phosphoric acid, one molecule of ribose (a pentose sugar), and one molecule of nitrogenous base. Depending on kinds of nitrogenous bases, ribonucleotides are divided into adenine ribonucleotides, guanine ribonucleotides, cytosine ribonucleotides, and uracil ribonucleotides.

2'-deoxyribonucleotide: it consists of one molecule of phosphoric acid, one molecule of 2'-deoxyribose (deoxylation of 2' of ribose, being a hydrogen atom), and one molecule of nitrogenous base. Depending on types of nitrogenous bases, natural 2'-deoxyribonucleotides are divided into adenine deoxyribonucleotides, guanine deoxyribonucleotides, cytosine deoxyribonucleotides, and thymine deoxyribonucleotides.

Non-natural nucleotide: it refers to a nucleotide derived from modification of the phosphate group, nitrogenous base, sugar ring and glycosidic bond of a natural nucleotide.

RNA: it refers to a molecule formed by natural or non-natural ribonucleotides linked by phosphoester bonds. Although typical RNA molecules are linked together by standard phosphodiester bonds, therapeutic RNAs may contain one or more non-standard bonds. RNA may be single-stranded or double-stranded, or may include both single-stranded and double-stranded regions. In addition, ribonucleotides can also be classified into linear ribonucleotide strands and circular ribonucleotide strands according to their morphology. The circular ribonucleotide strand consists of one or more linear ribonucleotide strands linked end-to-end by phosphoester bonds, and has a closed circular structure.

DNA: it refers to a molecule composed of 2'-deoxyribonucleotides linked by phosphoester bonds.

As used herein, "wild-type" refers to a form found in nature. For example, a wild-type protein sequence refers to a form that is found in nature, and can be isolated from a source in nature and has not been intentionally modified or altered by human.

The term "nick" herein refers to absence of a phosphodiester bond between two adjacent nucleotide fragments in a double-stranded structure. An intact phosphodiester bond may be formed by sealing the nick between a 3'-hydroxyl group of one nucleotide unit at the nick and a 5'-phosphate group of the other nucleotide unit at the nick, which is catalyzed by a double-stranded ligase. "Nick" can also be understood as a notch formed in a double-stranded nucleic acid molecule due to cleavage of a phosphodiester bond.

The term "gap" herein refers to such a case that a certain strand in a double-stranded structure is broken into two strands due to deletion of one or more contiguous nucleotides, and the two strands form a gap relationship.

A nucleic acid substrate herein refers to oligonucleotides capable of forming nicked double-stranded nucleic acid molecules, where the oligonucleotides contain a 5'-mono-phosphate group and/or a 3'-hydroxyl group.

The term "denaturation" herein refers to a process of disrupting hydrogen bonds between base pairs of double-stranded nucleic acids such as double-stranded DNA, double-stranded RNA or DNA/RNA through high-temperature incubation, causing the double-stranded nucleic acid to become single-stranded nucleic acid.

The term "annealing" herein refers to a process of gradually cooling a nucleic acid solution having undergone high-temperature denaturation to a low temperature to re-form single-stranded nucleic acid into double-stranded nucleic acid.

The term "percent sequence identity (%)" as used herein refers to comparisons among polynucleotides and polypeptides, and is determined by comparing two optimally aligned sequences over a comparison window, where a portion of a polynucleotide or polypeptide sequence in the comparison window may include additions or deletions (i.e., gaps) as compared to a reference sequence for optimal alignment of the two sequences. The percent may be calculated by determining the number of positions at which an identical nucleic acid base or amino acid residue occurs in two sequences to yield the number of matched positions, dividing the number of matched positions by the total number of positions in the comparison window, and multiplying the result by 100 to yield the percent sequence identity. Alternatively, the percent may be calculated by determining the number of positions at which either identical nucleic acid base or amino acid residue occurs in two sequences or the number of positions at which a nucleic acid base or amino acid residue is aligned with a gap to yield the number of matched positions, dividing the number of matched positions by the total number of positions in the comparison window, and multiplying the result by 100 to yield the percent sequence identity. Those skilled in the art could appreciate that there are currently many algorithms available to align sequences, such as the Smith-Waterman local homology algorithm (Smith and Waterman, Adv. Appl. Math., 2:482 [1981]) and Needleman-Wunsch global homology alignment algorithm (Needleman and Wunsch, J. Mol. Biol., 48:443 [1970]). These algorithms have been designed into relevant software by which researchers in the field can quickly align protein sequences or nucleotide sequences, such as the European Bioinformatics Institute (EMBL-EBI) open source software EMBOSS Water based on the Smith-Waterman algorithm and EMBOSS needle software based on the Needleman-Wunsch algorithm. Protein sequence alignment and sequence alignment identity % may be performed using the open software EMBOSS Water software. A scoring matrix employed during the alignment is BLOSUM62, with gap opening score (GAP OPEN) set to 10, and gap extension score (GAP EXTEND) set to 1.

"Reference sequence" refers to a specified sequence used as a basis for sequence comparison. The reference sequence may be a subset of a larger sequence, e.g., a segment of a full-length gene or polypeptide sequence. Generally, a reference sequence is at least 20 nucleotides or amino acid residues in length, at least 25 residues in length, at least 50 residues in length, at least 100 residues in length, or a full length of a nucleic acid or polypeptide. As two polynucleotides or polypeptides may each (1) contain a sequence (i.e., a portion of a complete sequence) that is similar between two sequences, and (2) may further contain a sequence that is divergent between two sequences, sequence comparison between two (or more) polynucleotides or polypeptides is typically performed by comparing sequences of the two polynucleotides or polypeptides over the "comparison window" so as to identify and compare local regions of sequence similarity. In some embodiments, the "reference sequence" can be based on a primary amino acid sequence, where the reference sequence is a sequence that can have one or more changes in the primary sequence.

The "comparison window" refers to a conceptual segment of at least approximately 20 contiguous nucleotide positions or amino acid residues where a sequence may be compared with a reference sequence of at least 20 contiguous nucleotides or amino acids, and where the portion of the sequence in the comparison window may include additions or deletions (i.e., gaps) of 20% or less as compared to the reference sequence (which does not include additions or deletions) for optimal alignment of the two sequences. The comparison window can be longer than 20 contiguous residues, and includes, optionally 30, 40, 50, 100, or longer windows.

"Corresponding to", "reference to", or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of T4 RNA ligase 2 mutants, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

In order to make objectives, technical solutions and advantages of embodiments in the present disclosure clearer, the technical solutions in the embodiments of the present disclosure will be described clearly and completely below. Embodiments, for which no concrete conditions are specified, are carried out according to conventional conditions or conditions recommended by manufactures. Where manufacturers of reagents or instruments used are not specified, they are conventional products commercially available.

In one aspect, embodiments of the present disclosure provide T4 RNA ligase 2 mutants. Compared with wild-type T4 RNA ligase 2, the T4 ligase 2 mutants have mutation at any one or more sites of positions 62, 103, 166, 168, 193, 217, 260, 297, 298, 303, 306, 311, 313 and 318 of an amino acid sequence of the wild-type T4 RNA ligase 2.

In some embodiments, having the mutation means that substitution or deletion of an amino acid residue occurs at corresponding site.

In some embodiments, the mutation at position 62 includes A62W, meaning that A at position 62 of the amino acid sequence is substituted with W; the mutation at position 103 includes P103G, meaning that P at position 103 of the amino acid sequence is substituted with G; the mutation at position 166 includes N166P, meaning that N at position 166 of the amino acid sequence is substituted with P; the mutation at position 168 includes L168F, meaning that L at position 168 of the amino acid sequence is substituted with F; the mutation at position 193 includes N193K, meaning that N at position 193 of the amino acid sequence is substituted with K; the mutation at position 217 includes any one of R217A, R217Q, R217N and R217P; the mutation at position 260 includes C260D; the mutation at position 297 includes T297A; the mutation at position 298 includes S298E; the mutation at position 303 includes T303D; the mutation at position 306 includes any one of Q306A, Q306D and Q306E; the mutation at position 311 includes any one of S311E, S311D, S311A and S311V; and the mutation at position 313 includes I313V.

In some embodiments, the T4 RNA ligase 2 mutants have any one or a combination of following mutations relative to the wild-type T4 RNA ligase 2: A62W, P103G, N166P, L168F, R217P, R217A, R217N, R217P, R217Q and C260D. The combination refers to a combination of any two or more, including any three, four and five thereof.

In some embodiments, the T4 RNA ligase 2 mutants have any one or a combination of following mutation combinations relative to the wild-type T4 RNA ligase 2: N193K-R217P, N193K-T297A, N193K-T303D, N193K-S311D, N193K-I313V. R217P-T297A, R217P-S298E, R217P-I313V, T297A-Q306D and S311E-I313V. The combination refers to a combination of any two or more thereof.

In some embodiments, the T4 RNA ligase 2 mutants have any one or a combination of following mutation combinations relative to the wild-type T4 RNA ligase 2: R217P-T297A-S311E, R217P-S298E-S311D, R217P-T297A-I313V, N193K-R217P-C260D, R217P-S311E-I313V, R217P-T303D-I313V, N193K-R217P-T303D-S311E, N193K-R217P-T303D-I313V, N193K-R217P-T303D-V318T, N193K-R217P-S311E-I313V, N193K-R217P-T303D-S311E-I313V, A62W-N193K-R217P-T303D-S311E-I313V, P103G-N193K-R217P-T303D-S311E-I313V, N166P-N193K-R217P-T303D-S311E-I313V, L168F-N193K-R217P-T303D-S311E-I313V, N193K-R217P-C260D-I303V-S311E-I313V-V318T, L168F-N193K-R217P-C260D-S311E-T303D-I313V-V318T, A62W-L168F-N193K-R217P-C260D-T303D-S311E-I313V-V318T, P103G-L168F-N193K-R217P-C260D-T303D-S311E-I313V-V318T, A62W-PI03G-L168F-N193K-R217P-C260D-T303D-S311E-I313V-V318T, A62W-P103G-N166P-L168F-N193K-R217P-C260D-T303D-S311E-I313V-V318T, A62W-N166P-L168F-N193K-R217P-C260D-T303D-S311E-I313V-V318T, P103G-N166P-L168F-N193K-R217P-C260D-T303D-S311E-I313V-V318T N166P-L168F-N193K-R217P-C260D-T303D-S311E-I313V-V318T. and In some embodiments, the T4 RNA ligase 2 mutants have any one of following mutation combinations relative to the wild-type T4 RNA ligase 2: N193K-R217P-C260D, R217P-S311E-I313V, N193K-R217P-T303D-S311E, N193K-R217P-T303D-V318T, N193K-R217P-S311E-I313V and N193K-R217P-T303D-S311E-I313V.

In some embodiments, the amino acid sequence of the wild-type T4 RNA ligase 2 has at least 80% identity to a sequence as set forth in SEQ ID NO: 1 or 2.

"Identity" refers to a sequence percent of two sequences that have identical nucleotide or amino acid residue at the same site. In some embodiments, "having at least 80% identity" specifically refers to having the identity of any one or within a range between any two of 80%, 82%, 84%, 86%, 88%, 90%, 92%, 94%, 96%, 98%, and 100%.

In some embodiments, the amino acid sequence of the wild-type T4 RNA ligase 2 is as set forth in SEQ ID NO: 1 or 2. SEQ ID NO: 1 (uniprot entry: P32277) and SEQ ID NO: 2 (D9IEL2 or A0A7S9SW04) are both T4 RNA ligase 2 sequences annotated in Uniprot database. A sequence difference between SEQ ID NO: 2 and SEQ ID NO: 1 is amino acid residue at position 112, where SEQ ID NO: 2 contains glycine, while SEQ ID NO: 1 contains cysteine, which is a normal phenomenon caused by protein sequence difference between different sequencing samples.

In some embodiments, a nucleic acid sequence encoding the amino acid sequence as set forth in SEQ ID NO: 1 is as set forth in SEQ ID NO: 3, and a nucleic acid sequence encoding the amino acid sequence as set forth in SEQ ID NO: 2 is as set forth in SEQ ID NO: 4.

In another aspect, embodiments of the present disclosure provide an isolated nucleic acid, encoding the T4 RNA ligase 2 mutants according to any one of the preceding embodiments. In addition, The degeneracy of the genetic code, where the same amino acids are encoded by alternative or synonymous codons, allows an extremely large number of nucleic acids to be made, all of which encode an engineered RNA ligase 2 variants of the present disclosure.

In another aspect, embodiments of the present disclosure further provide a vector, including the isolated nucleic acid according to any one of the preceding embodiments.

In another aspect, embodiments of the present disclosure further provide a host cell, including the vector according to any one of the preceding embodiments.

In another aspect, embodiments of the present disclosure further provide a preparation method for the T4 RNA ligase 2 mutants according to any one of the preceding embodiments, including: culturing the host cell according to any one of the preceding embodiments.

In another aspect, embodiments of the present disclosure further provide use of the T4 RNA ligase 2 mutants according to any one of the preceding embodiments in synthesis of nucleotide strands or in preparation of a product for synthesis of nucleotide strands of interest.

In another aspect, embodiments of the present disclosure provide a method for synthesizing a nucleotide strand of interest, including: performing a ligation reaction on a nicked double-stranded nucleic acid molecule and/or a nucleic acid substrate capable of forming the nicked double-stranded nucleic acid molecule under a condition of a first set temperature, where the first set temperature is ≥42° C.

In some embodiments, the first set temperature specifically may be any one or within a range between any two of 42, 45, 48, 50, 52, 55, 57, and 60° C.

In some embodiments, reaction duration under the condition of the first set temperature is ≥30 s.

In some embodiments, the reaction duration under the condition of the first set temperature ranges from 5 min to 16 h, and specifically may be any one or within a range between any two of 5 min, 10 min, 15 min, 20 min, 25 min, 30 min, 35 min, 40 min, 45 min, 50 min, 55 min, 60 min, 1 h, 2 h, 3 h, 4 h, 5 h, 6 h, 7 h, 8 h, 9 h. 10 h, 11 h, 12 h, 13 h, 14 h, 15 h, and 16 h.

In some embodiments, before, during and/or after the reaction under the condition of the first set temperature, the synthesizing method further includes performing a procedure of high-temperature denaturation-low-temperature annealing for at least one time, where the high-temperature denaturation includes performing a first incubation at a second set temperature, the second set temperature≥the first set temperature; and the low-temperature annealing includes performing a second incubation at a third set temperature, the third set temperature<the second set temperature.

In some embodiments, the second set temperature ranges from 42° C. to 60° C., and specifically may be any one or within a range between any two of 42, 44, 45, 46, 48, 50, 52, 54, 56, 58, and 60° C.

In some embodiments, the third set temperature is ≥4° C.

In some embodiments, the third set temperature is ≥any one of 4, 5, 6, 8, 10, 12, 14, 16, 18, 20, 22, 24, 26, 28, 30, 32, 34, 36, 38, and 40° C.

In some embodiments, the synthesizing method further includes: performing the procedure of high-temperature denaturation-low-temperature annealing for two or more times. The term "two or more times" as mentioned includes both exactly twice and any number of times greater than twice.

In some embodiments, duration of the first incubation is ≥30 s.

In some embodiments, the duration of the first incubation ranges from 5 min to 16 h, and specifically may be any one or within a range between any two of 5 min, 10 min, 15 min, 20 min, 25 min, 30 min, 35 min, 40 min, 45 min, 50 min, 55 min, 60 min, 1 h, 2 h, 3 h, 4 h, 5 h, 6 h, 7 h. 8 h, 9 h, 10 h. 11 h, 12 h, 13 h, 14 h, 15 h, and 16 h.

In some embodiments, duration of the second incubation is ≥30 s.

In some embodiments, the duration of the second incubation ranges from 5 min to 16 h, and specifically may be any one or within a range between any two of 5 min, 10 min, 15 min, 20 min, 25 min, 30 min, 35 min, 40 min, 45 min, 50 min, 55 min, 60 min, 1 h, 2 h, 3 h, 4 h. 5 h. 6 h, 7 h, 8 h, 9 h, 10 h, 11 h, 12 h, 13 h, 14 h, 15 h, and 16 h.

In another aspect, embodiments of the present disclosure provide a method for synthesizing a nucleotide strand of interest, including: performing a ligation reaction on a nicked double-stranded nucleic acid molecule and/or a nucleic acid substrate capable of forming the nicked double-stranded nucleic acid molecule, where during the ligation reaction, the procedure of high-temperature denaturation-low-temperature annealing according to any one of the preceding embodiments is performed for at least one time.

In some embodiments, the synthesizing method includes performing the procedure of high-temperature denaturation-low-temperature annealing for two or more times.

In some embodiments, the two or more times specifically include ≥2, 3, 4, 5, 6, 7, 8, 9, and 10 times.

The process of high-temperature denaturation-low-temperature annealing can eliminate nicked non-target double-stranded nucleic acid molecules or double-stranded nucleic acid molecule with "gaps" caused by mismatching, thereby improving the ligation efficiency and reducing the formation of ligation byproducts. In addition, since double-stranded structures are damaged by high temperature, direct reaction at high temperature may cause decreased ligation efficiency; therefore, by first raising the temperature to open nonspecific double-stranded nucleic acid, followed by annealing to a slightly low temperature, more nicked double-stranded molecules of interest can be formed and the nicks can be sealed, thus improving the ligation efficiency, and reducing the production of byproducts.

In some embodiments, the nicked double-stranded nucleic acid molecule includes any one or more of nicked RNA duplexes and nicked DNA/RNA hybrid duplexes.

In some embodiments, in the nicked double-stranded nucleic acid molecule, the term "nicked" may mean that at least one strand of the double-stranded nucleic acid molecule has at least one nick, that is, one strand may be nicked, or both strands may be nicked.

Specifically, the nicked DNA/RNA hybrid duplexes include at least one deoxyribonucleotide, and at least one nick has at least one end (3'-hydroxyl group and/or 5'-phosphate group) contains RNA.

In some embodiments, the nicked double-stranded nucleic acid molecule is linear and/or circular.

In some embodiments, the nicked double-stranded nucleic acid molecule is natural and/or modified.

In some embodiments, the nicked double-stranded nucleic acid molecule includes nucleic acid substrates or is formed by mixing the nucleic acid substrates or mixing and annealing the nucleic acid substrates.

In some embodiments, the nucleic acid substrate includes any one or more of the following: natural and/or modified RNA single strands, natural and/or modified RNA duplexes, natural and/or modified DNA single strands, natural and/or modified DNA/RNA hybrid single strands and natural and/or modified DNA/RNA hybrid duplexes.

In some embodiments, in the nucleic acid substrate, the RNA single strands include linear RNA single strands and/or circular RNA single strands, the RNA duplexes include linear RNA duplexes and/or circular RNA duplexes, the DNA single strands include linear DNA single strands and/or circular DNA single strands, the DNA/RNA hybrid single strands include linear DNA/RNA hybrid single strands and/or circular DNA/RNA hybrid single strands, and the DNA/RNA hybrid duplexes include linear DNA/RNA hybrid duplexes and/or circular DNA/RNA hybrid duplexes.

In some embodiments, the RNA single strands include any one or more of mRNA, antisense oligonucleotides, siRNA, sgRNA, lncRNA, CircRNA and miRNA.

When the nucleic acid substrate is double-stranded and nicked, the nucleic acid substrate itself is a nicked double-stranded nucleic acid molecule. When the nucleic acid substrate is single-stranded, the nicked double-stranded nucleic acid molecule can be formed by mixing the nucleic acid substrate with or without an annealing process.

In some embodiments, the nucleic acid substrate is annealed at a temperature ranging from 0° C. to 100° C., which specifically may be any one or within a range between any two of 0, 5, 10, 15, 20, 25, 30, 35, 40, 45, 50, 55, 60, 65, 70, 75, 80, 85, 90, 95, and 100° C.

In some embodiments, the process of forming the nicked double-stranded nucleic acid molecule with the nucleic acid substrate may occur in the process of mixing the nucleic acid substrate, without a separate heated annealing process. In this case the nucleic acid substrate, enzyme, ATP, Mg$^{2+}$ and other essential molecules and solutions for the reaction are directly mixed, during which the nucleic acid substrate specifically binds during the mixing, so as to form the nicked double-stranded nucleic acid molecule and start the ligation.

In some embodiments, the nucleic acid substrate has a fragment length of ≥2 nt.

In some embodiments, the fragment length of the nucleic acid substrate ranges from 2 nt to 200 nt, and specifically may be any one or within a range between any two of 2, 5, 7, 10, 13, 15, 17, 20, 23, 25, 27, 30, 33, 35, 37, 40, 43, 45, 47, 50, 53, 55, 57, 60, 63, 62, 67, 70, 73, 75, 77, 80, 85, 90, 100, 110, 120, 130, 140, 150, 160, 170, 180, 190, and 200 nt.

In some embodiments, the number of nucleic acid substrates is ≥1. When the nucleic acid substrate is a circular nicked double-stranded nucleic acid molecule, the number of nucleic acid substrates may be 1.

In some embodiments, the number of nucleic acid substrates is 1-50, and specifically may be any one or within a range between any two of 1, 2, 4, 6, 8, 10, 12, 14, 16, 18, 20, 22, 24, 26, 28, 30, 32, 34, 36, 38, 40, 42, 44, 46, 48, and 50.

The method in the present disclosure has no particular limitation on types of modifications, and all modification types are applicable. In some embodiments, the modification includes modification for enhancing stability and/or reducing innate immune response.

In some embodiments, the modification includes any one of modification of phosphate group, modification of base, modification of sugar ring and modification of glycosidic bond.

In some embodiments, the modification of phosphate group includes any one or more of the following: 5'-(E)-vinylphosphonate modification (5'-VP), phosphorothioate modification, phosphotriester modification, 5'-methylphosphonate modification, 5'-morpholino modification, phosphorodithioate modification, methoxypropyl phosphonate modification. S-5'-C-methyl analogue modification, short-chain alkyl or cycloalkyl intersugar bond modification, short-chain heteroatom or heterocyclic intersugar bond modification, or complete substitution of phosphate group with any one of amide, aminoxy, alkoxy and triazolyl.

In some embodiments, the modification of base includes any one or more of the following: 2,4-difluorotolylribonucleoside substitution, pseudouridine modification, 2-thiouridine modification, NI-methyl pseudouridine modification, 5-methyl uridine modification, 5-methoxyuridine modification, N6-methyl adenosine modification, N6,N6-dimethyladenosine modification, 3-methyluridine modification, N7-methylguanosine modification, 2,7-dimethylguanosine modification, 2,2,7-trimethylguanosine modification, 5-methylcytidine modification, 5-hydroxymethylcytosine modification, 5-bromo-uracil modification, 5-iodo-uracil modification, propynyluracil nucleoside modification, N-ethylpiperidine-6-triazole modified adenosine modification, 6'-phenylpyrrolocytosine modification. 2-aminopurine modification, inosine modification, 2,6-diaminopurine modification, 2-pyrimidone modification and 5-methylcytosine modification.

In some embodiments, the modification of sugar ring includes any one or more of the following: 2'-methoxy modification, 2'-deoxy-2'-fluoro modification, 2'-O-methoxyethyl modification, Locked Nucleic Acid (LNA) modification, Unlocked Nucleic Acid (UNA) modification, Bridged Nucleic Acid (BNA) modification, Tricyclo-DNA (tcDNA) modification, Phosphorodiamidate Morpholino Oligomer (PMO) modification, 2'-deoxynucleotide modification, (S)-constrained ethyl bicyclic nucleic acid modification, peptide nucleic acid modification and glycomimetic modification.

In some embodiments, the glycomimetic includes any one or more of the following: cyclobutyl in cyclobutyl nucleoside for replacing pentofuranosyl group, morpholinyl in morpholino nucleic acid (MNA), peptide backbone in peptide nucleic acid (PNA), polyethylene glycol backbone in glycol nucleic acid (GNA), threitol backbone in threose nucleic acid (TNA) and butyl backbone in acyclic nucleic acid (BuNA).

In some embodiments, the modification of glycosidic bond includes replacement of C—N bond in glycosidic linkage with any one of C—C, C—O and C—S.

In some embodiments, the nucleotide strand of interest has a sequence length ≥2 nt, 10 nt, 20 nt or 50 nt.

In some embodiments, the sequence length of the nucleotide strand of interest may range from 10 nt to 200 nt, and specifically may be any one or within a range between any two of 10, 20, 30, 40, 50, 60, 70, 80, 90, 100, 120, 140, 160, 180, and 200 nt.

In some embodiments, the nucleotide strand of interest is linear and/or circular.

In some embodiments, the nucleotide strand of interest is any one or more of RNA single strand, RNA duplex, DNA/RNA hybrid single strand and DNA/RNA hybrid duplex.

In some embodiments, the synthesizing method further includes isolating and purifying the ligated product, so as to obtain the nucleotide strand of interest.

In some embodiments, the synthesizing method further includes adding a ligase during the ligation reaction, where the ligase seals the nick by a phosphodiester bond.

In some embodiments, the ligase includes RNA ligases for ligating duplex.

In some embodiments, the ligases include RNA ligases of Rnl2 family and Rnl5 family.

In some embodiments, the ligases include: thermostable RNA ligases for ligating duplex. The thermostable ligases are ligases with high stability at a set temperature during ligation.

In some embodiments, the ligases include wild-type T4 RNA ligase 2 or mutants thereof. The wild-type T4 RNA ligase 2 or mutants thereof are the same as those described in any one of the preceding embodiments, and will not be reiterated herein.

In some embodiments, reaction duration of the synthesizing method is ≥5 min. In some embodiments, the reaction duration may range from 5 min to 16 h, and specifically may be any one or within a range between any two of 5 min, 30 min, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5 and 16 h.

In some embodiments, a system of the synthesis reaction includes: a nucleic acid substrate, enzyme, ATP and $Mg^{2+}$.

In another aspect, embodiments of the present disclosure further provide a kit, including a reagent for implementing the synthesizing method according to any one of the preceding embodiments.

In another aspect, embodiments of the present disclosure further provide use of a target reagent in preparation of a product for synthesizing nucleotide strands, where the target reagent is a reagent for implementing the synthesizing method according to any one of the preceding embodiments.

In some embodiments, the reagent for implementing the synthesizing method according to any one of the preceding embodiments includes the thermostable ligase according to any one of the preceding embodiments and a reaction solution for synthesizing nucleotide strands.

In some embodiments, the reaction solution for synthesizing nucleotide strands includes any one or more of 40-60 mM Tris-HCl (pH 7.8-8.2), 10-14 mM $MgCl_2$, 0.1-5 mM DTT, and 1-10 mM ATP. Each concentration is an action concentration of each component in the reaction system.

Specifically, the action concentration of Tris-HCl may be any one or within a range between any two of 40, 42, 44, 46, 48, 50, 52, 54, 56, 58, and 60 mM. The action concentration of $MgCl_2$ may be any one or within a range between any two of 10, 11, 11.5, 12, 12.5, 13, and 14 mM. The action concentration of DTT may be any one or within a range between any two of 0.1, 0.5, 1, 1.5, 2, 2.5, 3, 3.5, 4, 4.5, and 5 mM. The action concentration of ATP may be any one or within a range between any two of 1, 1.5, 2, 2.5, 3, 3.5, 4, 4.5, 5, 6, 7, 8, 9, and 10 mM.

In some embodiments, the ligase at a final concentration of 0.03-30 μM is added per 0.5-30 mM of the nucleic acid substrate. The 0.5-30 mM specifically may be any one or within a range between any two of 0.5, 1, 1.5, 1.6, 1.8, 2, 2.5, 3, 3.5, 4, 4.5, 5, 10, 15, 20, 25, and 30 mM. The 0.03-30 μM specifically may be any one or within a range between any two of 0.03, 0.04, 0.05, 0.1, 0.15, 0.2, 0.3, 0.4, 0.5, 0.6, 0.7, 0.8, 0.9, 1, 2, 3, 4, 5, 6, 7, 8, 9, 10, 15, 20, 25, and 30 μM.

Characteristics and performances of the present disclosure are further described in detail below in conjunction with examples.

Example 1; T4 Rnl2 Mutants

The present example obtained the wild-type T4 Rnl2 (amino acid sequence as set forth in SEQ ID NO: 2), and the wild-type T4 Rnl2 was engineered to obtain T4 Rnl2 mutants. Mutants relative to the wild type are as listed in Table 1 below.

TABLE 1

| T4 Rnl2 Mutants | |
| --- | --- |
| No. | Mutant |
| 1 | A76E |
| 2 | A62W |
| 3 | P103G |
| 4 | N166P |
| 5 | L168F |
| 6 | N193K |
| 7 | R217A |
| 8 | R217Q |
| 9 | R217N |
| 10 | R217P |
| 11 | C260D |
| 12 | T297A |
| 13 | S298E |
| 14 | T303D |
| 15 | Q306A |
| 16 | Q306D |
| 17 | Q306E |
| 18 | S311E |
| 19 | S311D |
| 20 | I313V |
| 21 | S311V |
| 22 | S311T |
| 23 | L317I |
| 24 | M320L |
| 25 | M320Y |
| 26 | N193K-S311D |
| 27 | N193K-S311E |
| 28 | N193K-Q306D |
| 29 | N193K-T303D |
| 30 | N193K-R217P |
| 31 | N193K-Q306E |
| 32 | N193K-S298E |
| 33 | R217P-S298E |
| 34 | N193K-T297A |
| 35 | T297A-S298B |
| 36 | S298E-S311E |
| 37 | T297A-Q306D |
| 38 | T297A-T303D |
| 39 | R217P-T297A |
| 40 | N193K-I313V |
| 41 | S298E-I313V |
| 42 | T297A-I313V |
| 43 | R217P-I313V |
| 44 | I313V-M320L |
| 45 | S311E-I313V |
| / | / |

Example 2: Engineering of T4 Rnl2 Recombinant Plasmids and Thermostable Mutant Plasmids (1) Cloning and Expression of T4 Rnl2 (Wild Type) and/or T4 Rnl2 Mutants Genes of T4 Rnl2 and/or engineered T4 Rnl2 mutants were cloned into pET-28a vector, with amino ends thereof being fused and expressed with a 10×His tag. Recombinant plasmids of each RNA ligase were transformed into expression strains BL21 (DE3). The expression strains were inoculated into LB liquid medium containing 50 mg/L kanamycin, and cultured overnight at 37° C. Subsequently, resultant was inoculated at a ratio of 1:20 into 400 mL of LB liquid medium supplemented with 50 mg/L kanamycin. 180 rpm shaking incubation was conducted at 37° C. until $OD_{600}$ reached 0.6-0.8, followed by cooling to 16° C. Isopropyl-β-D-thiogalactopyranoside (IPTG) at a final concentration of 0.5 mM was added, followed by 180 rpm shaking incubation at 16° C. for 20 h. After cultivation, bacterial cells were separated and harvested from 400 ml of the obtained culture by centrifugation at 8000 rpm for 5 min.

(2) Purification of T4 Rnl2 and Mutants Thereof

The bacterial cells were resuspended with 25 mL of membrane-rupture buffer (50 mM Tris 7.5, 150 mM NaCl, 10% glycerol, 0.5 mM DTT, 10 mM imidazole) and subjected to sonication disruption. Centrifugation was performed at 4° C. and 12,000 rpm for 20 min, to separate supernatant and pellet. Then the supernatant was well mixed with a pre-equilibrated nickel column, and incubated at 4° C. for 30 min. Subsequently, 30 mL of Wash buffer (50 mM Tris 7.5, 150 mM NaCl, 10% glycerol, 0.5 mM DTT, 20 mM imidazole) was added in three aliquots into a gravity column, to wash away non-specifically bound hybrid protein. Afterwards, 10 mL of Elution buffer (50 mM Tris 7.5, 150 mM NaCl, 10% glycerol (v/v), 0.5 mM DTT, 500 mM imidazole) was added in three aliquots into the gravity column to elute protein of interest. Then the protein eluted by the nickel column was added into a pre-treated dialysis bag, and transferred into 1× storage buffer (10 mM Tris 7.5, 50 mM KCl, 35 mM $(NH_4)_2SO_4$, 1 mM DTT, 1 mM EDTA, 50% (v/v) glycerol) for dialysis overnight. Finally, the protein was quantified by a BCA method.

Example 3: Thermal Stability Analysis of T4 Rnl2 Single-Site and Double-Site Mutants Temperature of melting (Tm) of T4 Rnl2 and mutants thereof was measured using SYPRO Orange (S5692, Merk) fluorescent staining method. This solution is a commonly used method for measuring thermal stability of protein, and reference can be made to relevant document for relevant principle and specific experimental steps (doi: 10.1002/0471140864.ps2809s79). In this example, fluorescent dye can bind to a hydrophobic region of protein to emit fluorescence. As the temperature rises, the protein was gradually unfolded, hydrophobic core was exposed, the quantity of fluorescence was gradually increased, and the Tm value of the protein can be calculated by sigmoid function fitting.

Figure 1:
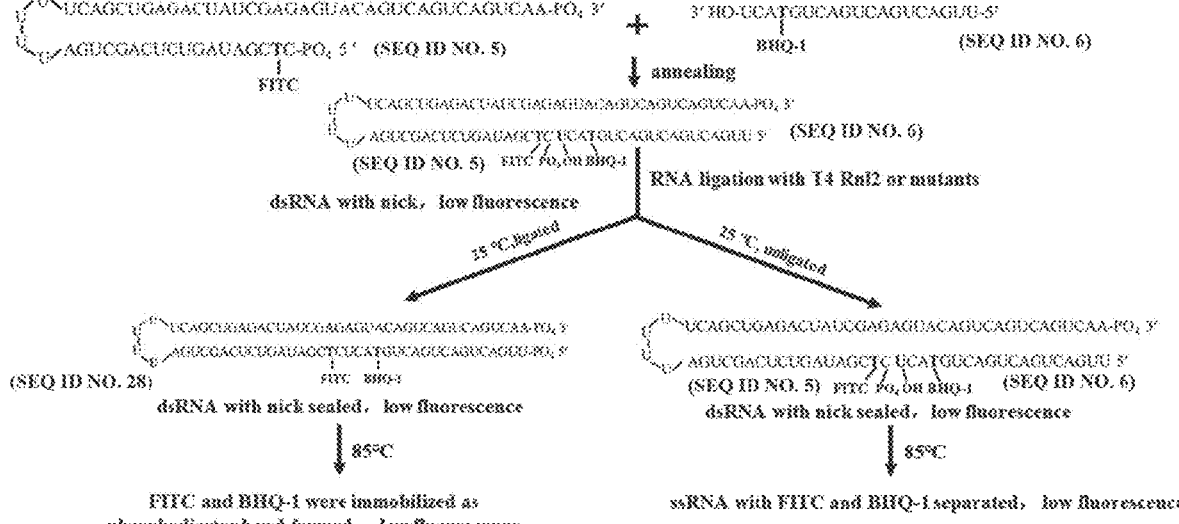
FIG. 1 is a schematic diagram of a solution for rapidly assessing RNA ligase activity.

Due to potential trade-offs between stability and activity, some mutations may adversely affect the activity of enzyme while improving the stability. Thus, in this example, the present study measured the ligase activity of the protein at 50° C. and 37° C. as another parameter to assess the thermal stability. Specifically, in order to rapidly assess the ligase activity of T4 Rnl2 mutants, the inventors designed a method for assessing RNA ligase activity based on the principle of fluorescence quenching on the basis of relevant document (doi: 10.1007/s00216-014-8351-1). See FIG. 1 for the principle of the solution.

More specifically, the inventors first designed two fluorescent probes: F1 fragment had a full length of 59 nt, and had 19-nt 5' end which can form a hairpin structure through reverse self-complementarity. Moreover, a second position from the 5' end was a FITC-labeled thymidine deoxythymidine (FITC-dT), and the remaining positions were all ribonucleotides. Both 5' and 3' of F1 fragment had a $PO_4$ group, where 5'-PO$_4$ group served as a donor in the ligation reaction, and adding 3'-PO$_4$ was to prevent intermolecular ligation between F1 fragments or self-circularization of F1. Moreover, F2 fragment with a full length of 19 nt can form complementary pairing with F1 fragment, and its 3'-OH provides an acceptor group in the ligation reaction. Moreover, a fourth position from 3' end of F2 fragment was a quencher BHQ-1-labelled thymidine deoxynucleotide (BHQ-1-dT), and the remaining positions were all ribonucleotides. Sequence of F1 was: 5'-C/iFITC-dT/CGAUA-GUCUCAGCUGAUUUUUCAGCUGAGACUAUCGAG-AGUACA GUCAGUCAGUCAA-3' (SEQ ID NO: 5); and sequence of F2 was: 5'-UUGACUGACUGACUG/iBHQ1dT/ACU-3' (SEQ ID NO: 6). F1 and F2 were mixed in equal proportions and then annealed as follows: firstly, mixed solution was incubated at 85° C. for 10 min, then slowly cooled to 37° C. and incubated for 10 min, subsequently incubated under a condition of 22° C. for 1 h, and finally cooled to 4° C. and incubated for 1 h. F1 and F2 after the annealing formed a nicked double-stranded RNA, and as the fluorophore and the quencher were close to each other, a fluorescence quenching effect was created. For a successfully ligated substrate (SEQ ID NO: 28), as the phosphodiester bond was formed, even if the temperature was raised, the fluorophore and the quencher were still close to each other, maintaining a fluorescence quenching state. For the substrate failed to be ligated, after the temperature was raised, as the base pairing was opened, the quencher and the fluorophore were separated, the fluorophore emitted fluoresce, and the quantity of fluorescence was increased. Afterwards, the ligation rate of T4 Rnl2 and its mutants under the current reaction conditions could be calculated based on reduced quantity of fluorescence. This example was specifically implemented as follows:

(1) Protein was diluted with 1× reaction buffer (50 mM Tris 8.0, 1 mM DTT, 0.4 mM ATP, 10 mM MgCl$_2$) to 0.05 mg/mL.

(2) Reaction system was prepared according to the following table, and the reaction system reacted at 37° C. and 50° C. for 1 h.

TABLE 2

Reaction Systems for Assessing Ligase Activity of T4 Rnl 2 and Mutants thereof

| Component | Control Group | Experimental Group | Final Concentration |
|---|---|---|---|
| DEPC water | 2 µL | 2 µL | — |
| 10 µM annealed | 2 µL | 2 µL | 2 µM |

TABLE 2-continued

Reaction Systems for Assessing Ligase Activity of T4 Rnl 2 and Mutants thereof

| Component | Control Group | Experimental Group | Final Concentration |
|---|---|---|---|
| double-stranded RNA | | | |
| 5× T4 Rnl2 Reaction Buffer | 2 µL | 2 µL | 1× |
| PEG 8000 (50%, w/v) | 2 µL | 2 µL | 10% (w/v) |
| Ligase (0.05 mg/mL) | 0 µL | 2 µL | 0.01 mg/mL |
| 1× reaction buffer | 2 µL | 0 µL | — |
| Total volume | 10 µL | 10 µL | — |

(3) Fluorescence detection and calculation of ligation rate: Fluorescence at 25° C. and 85° C. was detected with LightCycler® 96 fluorescence PCR thermocycler, and the ligation rate was calculated according to the following formula:

$$\text{Ligation efficiency} = \frac{[85° \text{ C. } FV(CG) - 25° \text{ C. } FV(CG)] - [85° \text{ C. } FV(EG) - 25° \text{ C. } FV(EG)]}{[85° \text{ C. } FV(CG) - 25° \text{ C. } FV(CG)]};$$

where "FV" is the abbreviation for "Fluorescence Value", "CG" is the abbreviation for "Control Group", and "EG" is the abbreviation for "Experimental Group".

$$\text{Residual activity} = \frac{\text{Ligation efficiency at } 50° \text{ C.}}{\text{Ligation efficiency at } 37.0° \text{ C.}}.$$

Figure 2:
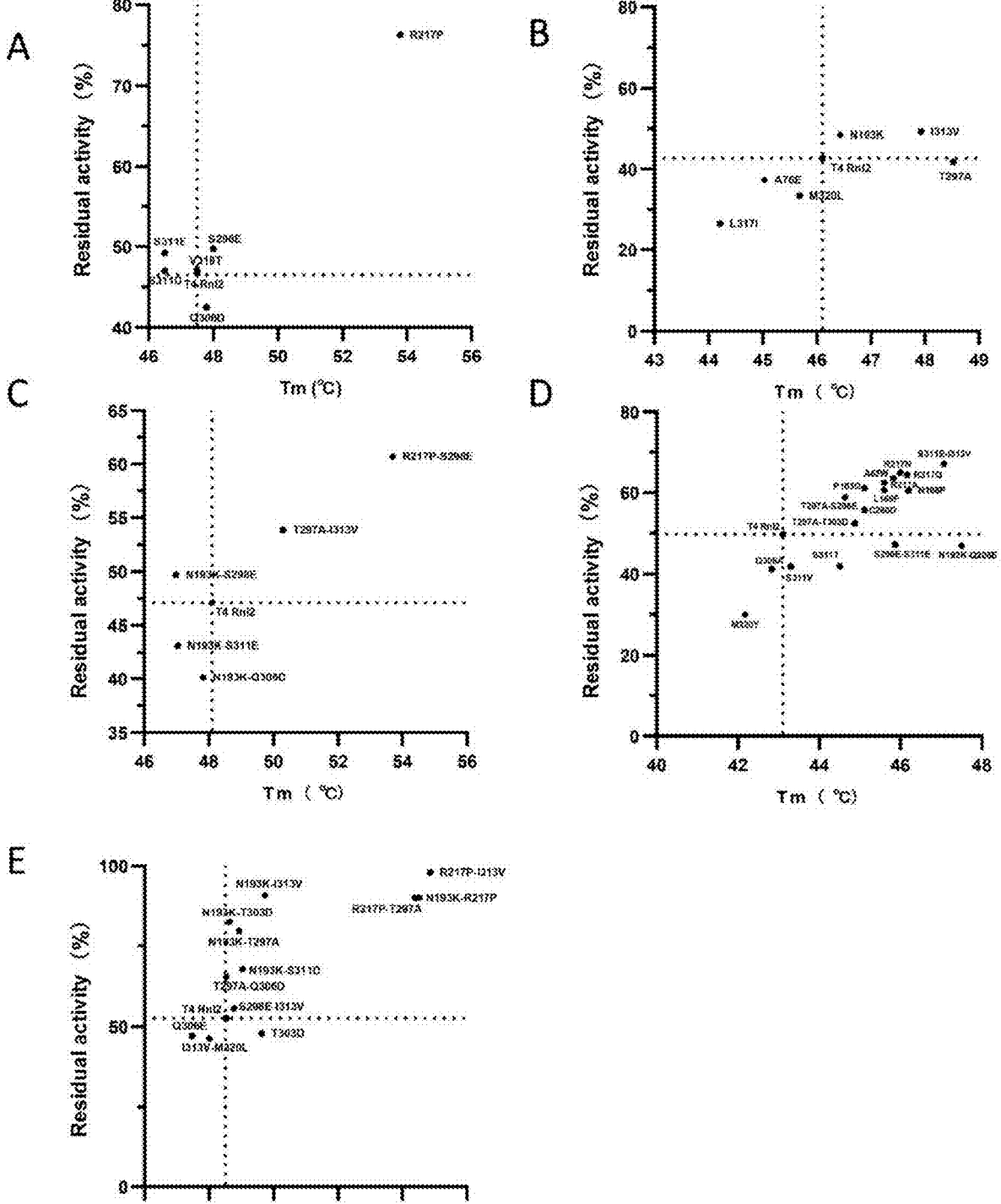
FIG. 2 is scatter diagrams of Tm values and residual activity of T4 Rnl2 single-site and double-site mutants, where A-E correspond to experimental batches 1-5.

Scatter diagrams (FIG. 2) were plotted with the measured protein Tm as X-axis, and the residual activity at 50° C. as Y-axis, and tabulated in Table 3. It should be noted that the experiment was conducted in batches, with potential differences between purified protein states in different batches and between experiment operations and assay, and thus T4 Rnl2 was taken as a reference in each batch of experiment.

Experimental results demonstrate that the Tm values of the mutants R217A/Q/N/P, P103G, N166P, L168F, A62W, C260D, N193K-R217P, R217P-T297A, R217P-S298E, R217P-I313V, and S311E-I313V were all elevated by ≥2.0° C., and the residual activity under a condition of 50° C. was enhanced by 10% or higher; although the Tm values of N193K-S311D, N193K-T297A, and N193K-I313V were not significantly elevated, the residual activity thereof were all enhanced by ≥15%. The results of this example demonstrate that the above T4 Rnl2 mutants could tolerate higher temperatures than the wild type.

TABLE 3

Tm Values and Residual Activity of T4 Rnl2 Single-site and Double-site Mutants

| Experimental Batch | Mutant | Tm (° C.) | ΔTm (° C.) | Residual Activity | Residual Activity Enhancement Value |
|---|---|---|---|---|---|
| 1 | T4 Rnl2 | 47.5 | 0.0 | 46.7% | 0.0% |
| | R217P | 53.8 | 6.3 | 76.3% | 29.6% |
| | S298E | 48.0 | 0.5 | 49.7% | 3.0% |
| | Q306D | 47.8 | 0.3 | 42.5% | −4.2% |
| | S311D | 46.5 | −1.0 | 47.0% | 0.3% |
| | S311E | 46.5 | −1.0 | 49.2% | 2.5% |
| | V318T | 47.5 | 0.0 | 47.1% | 0.4% |
| 2 | T4 Ral2 | 46.1 | 0.0 | 42.8% | 0.0% |
| | A76E | 45.0 | −1.1 | 37.3% | −5.4% |
| | N193K | 46.4 | 0.3 | 48.5% | 5.8% |
| | T297A | 48.5 | 2.4 | 41.9% | −0.9% |

TABLE 3-continued

Tm Values and Residual Activity of T4 Rnl2 Single-site and Double-site Mutants

| Experimental Batch | Mutant | Tm (° C.) | ΔTm (° C.) | Residual Activity | Residual Activity Enhancement Value |
|---|---|---|---|---|---|
| | I313V | 47.9 | 1.8 | 49.3% | 6.5% |
| | L3171 | 44.2 | −1.9 | 26.6% | −16.2% |
| | M320L | 45.7 | −0.4 | 33.4% | −9.4% |
| 3 | T4 Rnl2 | 43.1 | 0.0 | 49.8% | 0.0% |
| | R217A | 45.8 | 2.7 | 63.6% | 13.9% |
| | R217N | 46.0 | 2.9 | 65.0% | 15.3% |
| | R217Q | 46.2 | 3.1 | 64.5% | 14.7% |
| | C260D | 45.1 | 2.0 | 55.7% | 16.0% |
| | Q306A | 42.8 | −0.3 | 41.2% | −8.6% |
| | S311T | 44.5 | 1.4 | 41.9% | −7.8% |
| | S311V | 43.3 | 0.2 | 41.8% | −7.9% |
| | M320Y | 42.2 | −0.9 | 30.0% | −19.8% |
| | A62W | 45.5 | 2.4 | 62.5% | 12.8% |
| | P103G | 45.1 | 2.0 | 61.1% | 11.3% |
| | N166P | 46.2 | 3.1 | 60.5% | 10.7% |
| | L168F | 45.6 | 2.5 | 60.6% | 10.9% |
| | N193K-Q306E | 47.5 | 4.4 | 46.9% | −2.8% |
| | T297A-S298E | 44.6 | 1.5 | 58.8% | 9.1% |
| | T297A-T303D | 44.9 | 1.8 | 52.5% | 2.7% |
| | S298E-S311E | 45.9 | 2.8 | 47.2% | −2.5% |
| | S311E-I313V | 47.1 | 4.0 | 67.2% | 17.4% |
| 4 | T4 Rnl2 | 48.1 | 0.0 | 47.1% | 0.0% |
| | N193K-S298E | 47.0 | −1.1 | 49.7% | 2.6% |
| | N193K-S311E | 47.1 | −1.1 | 43.2% | −4.0% |
| | T297A-I313V | 50.3 | 2.2 | 53.9% | 6.7% |
| | R217P-S298E | 53.7 | 5.6 | 60.7% | 13.6% |
| | N193K-Q306D | 47.8 | −0.3 | 40.1% | −7.0% |
| 5 | T4 Rnl2 | 44.5 | 0.0 | 52.6% | 0.0% |
| | N193K-T297A | 44.9 | 0.4 | 79.6% | 27.0% |
| | N193K-R217P | 50.5 | 6.0 | 90.3% | 37.7% |
| | N193K-T303D | 44.6 | 0.1 | 82.6% | 30.0% |
| | N193K-I313V | 45.7 | 1.2 | 91.0% | 38.4% |
| | N193K-S311D | 45.0 | 0.5 | 67.9% | 15.3% |
| | Q306E | 43.5 | −1.1 | 47.2% | −5.4% |
| | R217P-T297A | 50.4 | 5.9 | 90.2% | 37.6% |
| | R217P-I313V | 50.9 | 6.3 | 98.1% | 45.5% |
| | T297A-Q306D | 44.5 | 0.0 | 65.5% | 12.9% |
| | S298E-I313V | 44.8 | 0.2 | 55.7% | 3.1% |
| | I313V-M320L | 44.0 | −0.5 | 46.4% | −6.3% |
| | T303D | 45.6 | 1.1 | 47.9% | −4.7% |

40

Example 4: Combinatorial T4 Rnl2 Mutant Engineering and Thermal Stability Analysis The present example provided the following mutants: R217P-T297A-S311E, R217P-S298E-S311D, R217P-T297A-I313V, N193K-R217P-C260D, R217P-S311E-I313V, R217P-T303D-I313V, N193K-R217P-T303D-S311E, N193K-R217P-T303D-I313V, N193K-R217P-T303D-V318T, A62W-N193K-R217P-T303D-S311E-I313V, N193K-R217P-S311E-I313V, N193K-R217P-T303D-S311E-I313V, P103G-N193K-R217P-T303D-S311E-I313V, N166P-N193K-R217P-T303D-S311E-I313V, L168F-N193K-R217P-T303D-S311E-I313V, N193K-R217P-C260D-T303D-S311E-I313V-V318T, L168F-N193K-R217P-C260D-S311E-T303D-I313V-V318T, A62W-L168F-N193K-R217P-C260D-T303D-S311E-I313V-V318T, P103G-L168F-N193K-R217P-C260D-T303D-S311E-I313V-V318T, A62W-P103G-L168F-N193K-R217P-C260D-T303D-S311E-I313V-V318T, A62W-P103G-N166P-L168F-N193K-R217P-C260D-T303D-S311E-I313V-V318T, A62W-N166P-L168F-N193K-R217P-C260D-T303D-S311E-I313V-V318T, P103G-N166P-L168F-N193K-R217P-C260D-T303D-S311E-I313V-V318T and N166P-L168F-N193K-R217P-C260D-T303D-S311E-I313V-V318T. The mutants were derived from the wild-type T4 Rnl2, with the amino acid sequence as set forth in SEQ ID NO: 2.

The specific vector engineering scheme and protein purification method were the same as those in Example 2, and the method for determining the Tm value was the same as that in Example 3. The activity assay scheme was substantially identical to Example 3, with a slight difference that during activity assay, protein was first diluted with 1× reaction buffer (50 mM Tris 8.0, 1 mM DTT, 0.4 mM ATP, 10 mM MgCl₂) to 0.05 mg/mL, and incubated respectively at 37° C. and 45° C. for 1 h. Subsequently, the protein after thermal incubation was added into the reaction system, to react respectively at 37° C. and 45° C. for 1 h, and finally fluorescence was measured, and the ligation rate and residual activity were calculated. Results of Tm values and activity assay were shown in FIG. 3, and relevant data were listed in Table 4, where T4 Rnl2 and R217P-I313V mutant that performed best during single-site and double-site mutant screening were used as controls.

Experimental results demonstrate that all the multi-site mutants, including R217P-T297A-S311E, R217P-S298E-S311D, R217P-T297A-I313V, N193K-R217P-C260D, R217P-S311E-I313V, R217P-T303D-I313V, N193K-R217P-T303D-S311E, N193K-R217P-T303D-I313V, N193K-R217P-T303D-V318T, N193K-R217P-S311E-I313V, N193K-R217P-T303D-S311E-I313V, A62W-N193K-R217P-T303D-S311E-I313V, P103G-N193K-R217P-T303D-S311E-I313V, N166P-N193K-R217P-

Figure 3:
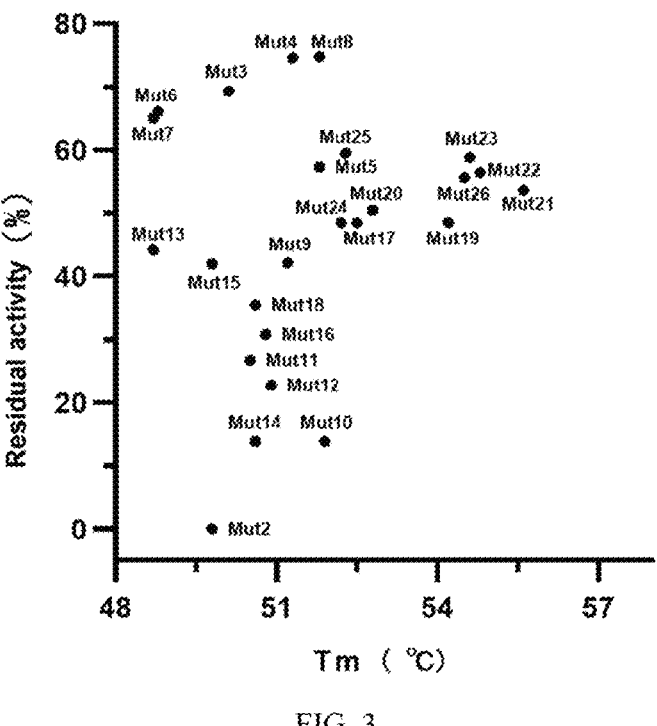
FIG. 3 is a scatter diagram of Tm values and residual activity of T4 Rnl2 multi-site combinatorial mutants.

T303D-S311E-I313V, L168F-N193K-R217P-T303D-S311E-I313V, N193K-R217P-C260D-T303D-S311E-I313V-V318T, L168F-N193K-R217P-C260D-S311E-T303D-I313V-V318T, A62W-L168F-N193K-R217P-C260D-T303D-S311E-I313V-V318T, P103G-L168F-N193K-R217P-C260D-T303D-S311E-I313V-V318T, A62W-P103G-L168F-N193K-R217P-C260D-T303D-S311E-I313V-V318T, A62W-P103G-N166P-L168F-N193K-R217P-C260D-T303D-S311E-I313V-V318T, A62W-N166P-L168F-N193K-R217P-C260D-T303D-S311E-I313V-V318T, P103G-N166P-L168F-N193K-R217P-C260D-T303D-S311E-I313V-V318T and N166P-L168F-N193K-R217P-C260D-T303D-S311E-I313V-V318T exhibited higher residual activity (FIG. 3). In the above, six multi-site mutants, including N193K-R217P-C260D, R217P-S311E-I313V, N193K-R217P-T303D-S311E, N193K-R217P-T303D-V318T, N193K-R217P-S311E-I313V, and N193K-R217P-T303D-S311E-I313V, were particularly outstanding, with the residual activity >60%.

Example 5: Activity Analysis for T4 Rnl2 Mutants at Different Temperatures

The present example analyzed the thermal stability of T4 Rnl2 and its mutants N193K-R217P (Mut1), R217P-I313V (Mut2), N193K-R217P-C260D (Mut3), R217P-S311E-I313V (Mut4), N193K-R217P-T303D-S311E (Mut5), N193K-R217P-S311E-I313V (Mut6), N193K-R217P-T303D-V318T (Mut7), and N193K-R217P-T303D-S311E-I313V (Mut8) at different temperatures. This example was specifically implemented as follows.

(1) Protein was diluted with 1× reaction buffer (50 mM Tris 8.0, 1 mM DTT, 0.4 mM ATP, 10 mM $MgCl_2$) to 0.05 mg/mL, and incubated respectively at 35.7° C., 37.0° C., 42.6° C., 45.1° C., 48.1° C., 50.6° C. and 54.7° C. for 1 h.

(2) Reaction systems were prepared according to the following table, and the reaction systems reacted at corresponding temperatures (35.7° C., 37.0° C., 42.6° C., 45.1° C., 48.1° C., 50.6° C. and 54.7° C.) of protein incubation for 1 h.

TABLE 4

Thermal Stability Analysis for T4 Rnl2 and Mutants thereof

| | Mutant | Tm (° C.) | ΔTm (° C.) | Residual Activity | Residual Activity Enhancement Value |
|---|---|---|---|---|---|
| Mut2 | R217P-I313V | 49.8 | 0 | 0.0% | 0.0% |
| Mut3 | N193K-R217P-C260D | 50.1 | 0.3 | 69.3% | 69.3% |
| Mut4 | R217P-S311E-I313V | 51.3 | 1.5 | 74.6% | 74.6% |
| Mut5 | N193K-R217P-T303D-S311E | 51.8 | 2.0 | 57.3% | 57.3% |
| Mut6 | N193K-R217P-S311E-I313V | 48.8 | −1.0 | 66.1% | 66.1% |
| Mut7 | N193K-R217P-T303D-V318T | 48.7 | −1.1 | 65.0% | 65.0% |
| Mut8 | N193K-R217P-T303D-S311E-I313V | 51.8 | 2.0 | 74.8% | 74.8% |
| Mut9 | L168F-N193K-R217P-T303D-S311E-I313V | 51.2 | 1.4 | 42.1% | 42.1% |
| Mut10 | R217P-T297A-S311E | 51.9 | 2.1 | 13.8% | 13.8% |
| Mut11 | R217P-S298E-S311D | 50.5 | 0.7 | 26.7% | 26.7% |
| Mut12 | R217P-T297A-I313V | 50.9 | 1.1 | 22.7% | 22.7% |
| Mut13 | R217P-T303D-I313V | 48.7 | −1.1 | 44.1% | 44.1% |
| Mut14 | N193K-R217P-T303D-I313V | 50.6 | 0.8 | 13.8% | 13.8% |
| Mut15 | A62W-N193K~R217P-T303D-S311E-I313V | 49.8 | 0.0 | 41.9% | 41.9% |
| Mut16 | P103G-N193K-R217P-T303D-S311E-I313V | 50.8 | 1.0 | 30.8% | 30.8% |
| Mut17 | N166P-N193K-R217P-T303D-S311E-I313V | 52.5 | 2.7 | 48.5% | 48.5% |
| Mut18 | N193K-R217P-T303D-S311E-I313V-C260D-V318T | 50.6 | 0.8 | 35.4% | 35.4% |
| Mut19 | L168F-N193K-R217P-C260D-S311E-T303D-I313V-V318T | 54.2 | 4.4 | 48.5% | 52.5% |
| Mut20 | A62W-L168F-N193K-R217P-C260D-T303D-S311E-I313V-V318T | 52.8 | 3.0 | 50.5 | 50.5% |
| Mut21 | P103G-L168F-N193K-R217P-C260D-T303D-S311E-I313V-V318T | 55.6 | 5.8 | 53.6 | 53.6% |
| Mut22 | A62W-P103G-L168F-N193K-R217P-C260D-T303D-S311E-I313V-V318T | 54.8 | 5.0 | 56.4 | 56.4% |
| Mut23 | A62W-P103G-N166P-L168F-N193K-R217P-C260D-T303D-S311E-I313V-V318T | 54.6 | 4.8 | 58.8 | 58.8% |
| Mut24 | A62W-N166P-L168F-N193K-R217P-C260D-T303D-S311E-I313V-V318T | 52.2 | 2.4 | 48.5 | 48.5% |
| Mut25 | P103G-N166P-L168F-N193K-R217P-C260D-T303D-S311E-I313V-V318T | 52.3 | 2.5 | 59.5 | 59.5% |
| Mut26 | N166P-L168F-N193K-R217P-C260D-T303D-S311E-I313V-V318T | 54.5 | 4.7 | 55.6 | 55.6% |

TABLE 5

Reaction Systems for Assessing Ligase Activity of
T4 Rnl 2 and Mutants thereof

| Component | Control Group | Experimental Group | Final Concentration |
|---|---|---|---|
| DEPC water | 2 μL | 2 μL | — |
| 10 μM annealed double-stranded RNA | 2 μL | 2 μL | 2 μM |
| 5× T4 Rnl2 Reaction Buffer | 2 μL | 2 μL | 1× |
| PEG 8000 (50%, w/v) | 2 μL | 2 μL | 10% (w/v) |
| Ligase (0.05 mg/mL) | 0 μL | 2 μL | 0.01 mg/mL |
| 1× reaction buffer | 2 μL | 0 μL | — |
| Total volume | 10 μL | 10 μL | — |

(3) Fluorescence detection and calculation of ligation rate:
Fluorescence at 25° C. and 85° C. was detected with
LightCycler® 96 fluorescence PCR thermocycler, and
the ligation rate was calculated according to the following formula:

$$\text{Ligation efficiency} = \frac{[85°\text{ C. } FV(CG) - 25°\text{ C. } FV(CG)] - \frac{85°\text{ C. } FV(EG) - 25°\text{ C. } FV(EG)]}{[85°\text{ C. } FV(CG) - 25°\text{ C. } FV(CG)]}}{[85°\text{ C. } FV(CG) - 25°\text{ C. } FV(CG)]};$$

where "FV" is the abbreviation for "Fluorescence Value",
"CG" is the abbreviation for "Control Group", and "EG" is
the abbreviation for "Experimental Group".

$$\text{Residual activity} = \frac{\text{Ligation efficiency at different temperatures}}{\text{Ligation efficiency at 37.5° C.}}.$$

Figure 4:
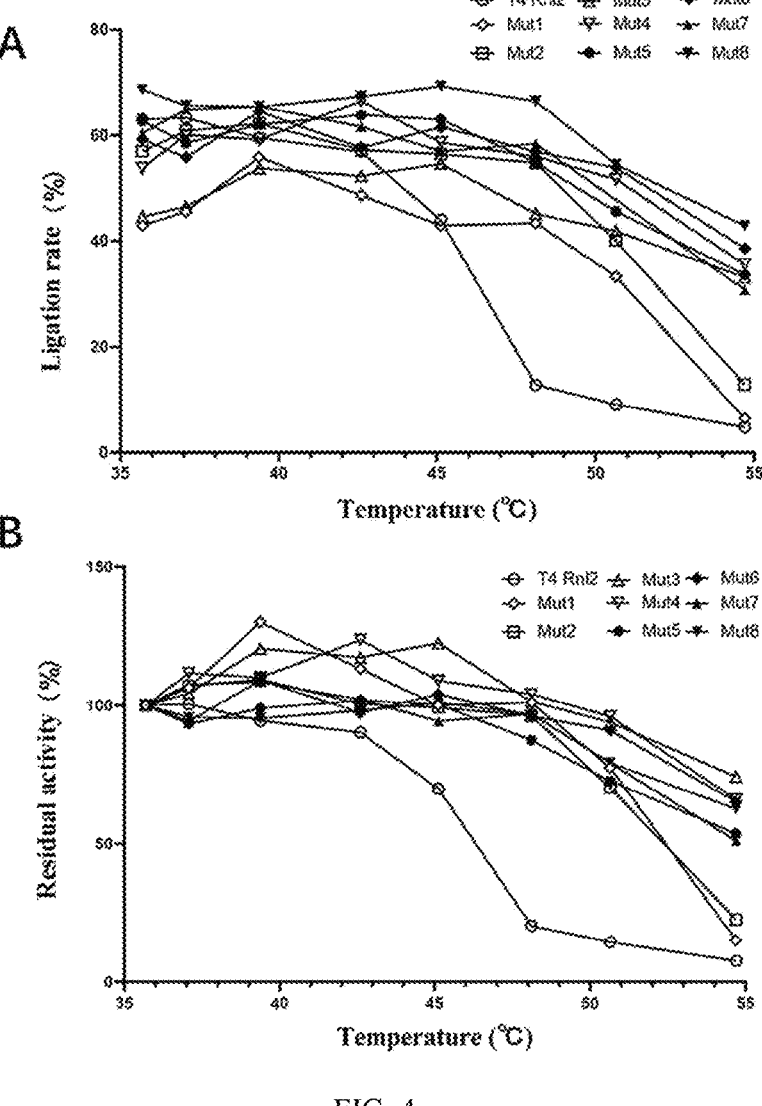
FIG. 4 shows ligase activity of T4 Rnl2 ligase mutants at different temperatures.

Results of RNA ligation rates and residual activity of T4
Rnl2 and its mutants after 1 h of reaction at different
temperatures were respectively shown by A and B in FIG. 4.
After 1 h of treatment at 48.1° C., the ligation rate of T4 Rnl2
was only 12.8%, the residual activity was 20.3%; while
under the same condition, Mut1-8 achieved the ligation rate
between 43.4% and 66.5%, and the residual activity reached
87.4%-100% (Table 6). By further comparing the ligation
rates of different mutants at higher temperatures, it can be
found that after 1 h of treatment at 54.7° C., the ligation rates
of Mut1 and Mut2 were respectively 6.5% and 12.5%, and
the residual activity was respectively 15.1% and 22.6%;
while after treatment under the same condition, Mut3-8 still
had the ligation rate of ~40%, and the residual activity was
53.6-74.2% or above (Table 6).

TABLE 6

Ligation Rates and Residual Activity of T4 Rnl2
and Mutants thereof at Different Temperatures

| | 35.7° C. | 48.1° C. | | 54.7° C. | |
| Protein | Ligation Rate | Ligation Rate | Residual Activity | Ligation Rate | Residual Activity |
|---|---|---|---|---|---|
| T4 Rnl2 | 63.1% | 12.8% | 20.3% | 4.8% | 7.6% |
| Mut1 | 43.0% | 43.4% | 101.0% | 6.5% | 15.1% |
| Mut2 | 57.0% | 54.8% | 96.2% | 12.9% | 22.6% |
| Mut3 | 44.6% | 45.2% | 101.3% | 33.1% | 74.2% |
| Mut4 | 53.9% | 56.0% | 104.0% | 35.6% | 66.1% |
| Mut5 | 62.8% | 54.9% | 87.4% | 33.7% | 53.6% |
| Mut6 | 59.2% | 56.9% | 96.1% | 38.6% | 65.2% |

TABLE 6-continued

Ligation Rates and Residual Activity of T4 Rnl2
and Mutants thereof at Different Temperatures

| | 35.7° C. | 48.1° C. | | 54.7° C. | |
| Protein | Ligation Rate | Ligation Rate | Residual Activity | Ligation Rate | Residual Activity |
|---|---|---|---|---|---|
| Mut7 | 60.4% | 58.4% | 96.8% | 30.8% | 51.0% |
| Mut8 | 68.7% | 66.5% | 96.8% | 42.9% | 62.5% |

The present example further analyzed the thermal stability
of relevant mutants by a denaturing gel electrophoresis
method.

First, the protein was diluted to 0.5 mg/mL, and then
heated at 45° C. for 1 h and 16 h or at 50° C. for 1 h and 4
h, respectively. Subsequently, centrifugation was performed
at 12000 rpm for 10 min, supernatant was taken to prepare
an SDS-PAGE sample, and SDS-PAGE denaturing gel elec-
trophoresis was performed. Results of SDS-PAGE (A and B
in FIG. 5) demonstrate that, for T4 Rnl2, after 1 h of heating
at 45° C., ~10% of the protein remained in the supernatant,
and after 16 h of heating at 45° C. for or 1 h of heating at
50° C., the protein almost completely precipitated, and the
supernatant was almost free of protein; for Mut1, after 1 h
of heating at 45° C., ~40% of the protein remained in the
supernatant, and after 16 h of heating at 45° C. or 1 h of
heating at 50° C., ~10% of the protein remained in the
supernatant; for Mut2 and Mut4, after 1 h of heating at 45°
C., still ~70% of the protein remained in the supernatant,
after 16 h of heating at 45° C., still ~40% of the protein
remained in the supernatant, after 1 h of heating at 50° C.,
~10% of the protein remained in the supernatant; for Mut3,
Mut5, Mut6, Mut7, and Mut8, even after 16 h of heating at
45° C., there was still about 70% of the protein in the
supernatant, and after 4 h of heating at 50° C., there was still
about 50% of the protein in the supernatant.

Example 6: T4 Rnl2 Mutants Ligated 4 Fragments of Non-Natural RNAs at High Temperatures Non-natural modifications can enhance stability of RNA
and reduce immunogenicity of RNA. Therefore, some non-
natural modifications are added to small RNAs and mRNAs
currently used. In the present example, the screened ther-
mostable mutants were used to ligate non-natural RNAs.

9 thermostable RNA ligases (Mut1-9) prepared were
measured for ligase activity under the following conditions.
4 fragments of oligonucleotides in Table 7 were taken as
substrates. As shown in FIG. 6, the 4 fragments of oligo-
nucleotides were ligated, and subjected to reaction to gen-
erate complementary RNA fragments (SEQ ID NO: 29 and
SEQ ID NO: 30). For convenience, RNA generated from
ligation reaction of F1 and F2 is designated as sense strand
(abbreviated as SS, SEQ ID NO: 29), and RNA generated
from F3 and F4 is designated as antisense strand (abbrevi-
ated as AS, SEQ ID NO: 30).

20 μL of reaction solution containing various oligonucle-
otide fragments at a final concentration of 1.6 mM for each,
50 mM Tris-HCl (pH 8.0), 12 mM MgCl₂, 1 mM DTT, 4
mM ATP and 0.005 mg/mL of each enzyme was added into
a 200 μL microtube, and subjected to the ligation reaction
respectively at 37° C., 42° C., 45° C., and 50° C. maintained
by a PCR thermocycler. 4 h after initiation of the reaction,
1 μL of the reaction solution was sampled and 49 μL of a 10
mM EDTA solution was added to terminate the reaction.
Finally, product was analyzed using HPLC, and a proportion
of the product was calculated by dividing peak areas of the
SS+AS strands in HPLC chromatogram by a total peak area of nucleotides in a whole chromatogram, and the residual activity was calculated as follows:

$$\text{Product proportion} = \frac{\text{Area}(AS + SS)}{\text{Area}(F1 \sim 4 + AS + SS)};$$

$$\text{Residual activity} = \frac{\text{Product proportion at } 50^\circ \text{ C.}}{\text{Product proportion at } 37^\circ \text{ C.}}.$$

TABLE 7

Oligonucleotide Fragments Used in Ligation Reaction of 4 Fragments

| Fragment | Name | Sequence | SEQ ID NO: |
|---|---|---|---|
| SS strand 5' end | F1 | fU-fA-mG-fA-mC-fC-mC-mG-f-mA-mC-fA | 7 |
| SS strand 3' end | F2 | Pho-mU-fG-mU-mU-fC-fC-mG | 8 |
| AS strand 5' end | F3 | fC-mG-fG-mA-mA-fC-mA-fU-fG-mU-fC | 9 |
| AS strand 3' end | F4 | Pho-mG-fG-fG-fU-mC-fU-mA | 10 |

Note: "Pho" represents 5'-terminus phosphate group; "f" represents modification with 2'-fluoro group; "m" represents modification with 2'-O-methyl; and "-" represents phosphodiester bond.

Results of the example are listed in Table 8.

TABLE 8

| | T4 Rnl2 Mutants Ligating 4 Fragments of Non-natural RNAs at High Temperatures | | | |
|---|---|---|---|---|
| Variant | 37° C. AS + SS (%) | 42° C. AS + SS (%) | 45° C. AS + SS (%) | 50° C. AS + SS (%) |
| T4 Rnl2 | 39.3 | 52.3 | 33.5 | 6.8 |
| Mut 1 | 47.6 | 77.1 | 76.7 | 57.3 |
| Mut2 | 45.5 | 70.2 | 60.7 | 33.5 |
| Mut3 | 48.1 | 96.2 | 96.2 | 95.8 |
| Mut4 | 47.4 | 74.9 | 64.2 | 32.7 |
| Mut5 | 48.1 | 84.2 | 77.7 | 54.8 |
| Mut6 | 48.0 | 86.2 | 81.0 | 56.5 |
| Mut7 | 47.5 | 78.1 | 71.5 | 51.3 |
| Mut8 | 47.6 | 70.1 | 65.7 | 50.8 |
| Mut9 | 46.8 | 72.5 | 68.5 | 65.4 |

Under the condition of 42° C., the ligation rates of T4 Rnl2 and its mutants Mut1-8 were all higher than those at 37° C., the ligation rates of Mut1, Mut2, Mut4, Mut7 and Mut8 were all >70%, and the ligation rates of Mut3, Mut5 and Mut6 were >80%. Under the condition of 45° C., the ligation rates of Mut2, Mut4, and Mut8 were all >60%, the ligation rates of Mut1, Mut5 and Mut7 were all >70%, the ligation rate of Mut6 was ~81%, and the ligation rate of Mut3 was ~96%. Under the condition of 50° C., the ligation rate of T4 Rnl2 was substantially lost, being <10%, Mut2 still maintained the ligation rate of ~34%, the ligation rates of Mut1, Mut5, Mut6, Mut7, and Mut8 were >50%, and the ligation rate of Mut3 was >96%.

Example 7: T4 Rnl2 Ligase Mutants Reacted at High Temperatures, with Reduced Production of Byproducts Thermostable T4 Rnl2 mutant N193K-R217P-C260D (Mut3) provided in Example 4 was used as ligase to ligate nucleic acid substrates, so as to synthesize nucleotide strands.

Specifically, the nucleic acid substrates included 4 fragments, specifically listed in Table 9, and a schematic diagram of ligation is as shown in FIG. 7. According to FIG. 7, F2-1 (Experimental Group 1), F2-2 (Experimental Group 2), and F2-3 (Experimental Group 3) respectively had a pairing region of 3 nt, 2 nt and 1 nt and an unpaired region of 4 nt, 5 nt and 6 nt with F1. Mismatching structures between F3 and F2 fragments resulted in mistaken or undesired ligation between F2 and F3. For descriptive convenience, F1 oligonucleotide is designated as sense strand (abbreviated as SS), and oligonucleotide generated from F2 and F3 is designated as antisense strand (abbreviated as AS, SEQ ID NO: 31, SEQ ID NO: 32, and SEQ ID NO: 33).

TABLE 9

Nucleic Acid Substrates Used in Example 7

| Fragment | Name | Sequence | SEQ ID NO: |
|---|---|---|---|
| SS strand | F1 | G-A-A-C-U-U-G-G-A-C-A-G-A-A-U | 11 |
| AS strand 3' end | F3 | Pho-C-C-A-A-G-U-U-C | 12 |
| AS strand 5' end | F2-1 (Experimental Group 1) | C-C-A-A-U-G-U | 13 |
| | F2-2 (Experimental Group 2) | C-C-A-A-A-G-U | 14 |
| | F2-3 (Experimental Group 3) | C-C-A-A-A-A-U | 15 |

Note: "Pho" represents 5'-terminus phosphate group; and "-" represents phosphodiester bond.

Synthesis of the nucleotide strands included: 20 µL of reaction solution containing various oligonucleotides at a final concentration of 1.6 mM for each, 50 mM Tris-HCl (pH 8.0), 12 mM MgCl$_2$, 1 mM DTT, 4 mM ATP and 0.005 mg/mL of enzyme was added into a 200 μL microtube, and subjected to the ligation reaction respectively at 37° C. and 50° C. maintained by a PCR thermocycler. 4 h and 16 h after initiation of the reaction, 1 μL of the reaction solution was sampled and 49 μL of a 10 mM EDTA solution was added to terminate the reaction. Finally, product was separated using HPLC, and components of each peak were analyzed using mass spectrometry. A proportion of the product was calculated by dividing peak areas of various products in HPLC chromatogram by a total peak area of oligoribonucleotides in a whole chromatogram, that is:

$$\text{Proportion of mistakenly ligated product} = \frac{\text{Area}(F2 + F3)}{\text{Area}(F1 \sim 3 + AS + SS + \text{byproduct})}$$

Results of the example are listed in Table 10.

TABLE 10

Production of Mistakenly ligated Products
(F2 + F3) at Different Reaction Temperatures

| | 37° C.-4 h | 50° C.-4 h | 37° C.-16 h | 50° C.-16 h |
|---|---|---|---|---|
| Experimental Group 1 | 16.2% | 4.1% | 23.0% | 6.0% |
| Experimental Group 2 | 17.2% | 2.6% | 23.4% | 4.4% |
| Experimental Group 3 | 10.0% | 1.2% | 17.7% | 2.9% |

After 4 h of reaction under the condition of 37° C., proportions of the mistakenly ligated products produced in the three experimental groups were 16.2%, 17.2% and 10.0%, respectively; after 4 h of reaction under the condition of 50° C., proportions of the ligated products caused by mismatch were 4.1%, 2.6% and 1.2%, respectively. After 16 h of reaction under the condition of 37° C. proportions of the products caused by mismatch in the three experimental groups were 23.0%, 23.4% and 17.7%, respectively; and after 4 h of reaction under the condition of 50° C., proportions of the the products caused by mismatch were 6.0%, 4.4% and 2.9%, respectively.

Results demonstrate that at 50° C., using the thermostable T4 Rnl2 ligase mutants for high-temperature reaction can significantly reduce the generation of products caused by mismatch.

Example 8: T4 Rnl2 Ligase Mutants Ligated Double-Stranded RNA Sequences at High Temperatures, with Reduced Production of Byproducts Thermostable T4 Rnl2 mutants N193K-R217P-C260D (Mut3) and N193K-R217P-S311E-I313V (Mut6) and L168F-N193K-R217P-T303D-S311E-I313V (Mut9) in Example 4 were used as ligases, and 4 fragments in Table 11 were used as nucleic acid substrates, to synthesize nucleotide strands, with a schematic diagram of the ligation as shown in FIG. 8. As a control experimental group, purified T4 Rnl2 (wild type) was used to react in the control group under the same conditions. For descriptive convenience, oligonucleotide generated through ligation reaction of F1 and F2 is designated as sense strand (abbreviated as SS, SEQ ID NO: 34), and oligonucleotide generated from F3 and F4 is designated as antisense strand (abbreviated as AS, SEQ ID NO: 35).

TABLE 11

Nucleic Acid Substrates Used in Ligation Reaction in Example 8

| Fragment | Name | Sequence | SEQ ID NO: |
|---|---|---|---|
| SS strand 5' end | F1 | Pho-A-C-G-C-A-U-G-A | 16 |
| SS strand 3' end | F2 | Pho-A-C-U-G-C-U-A-C-U-U-A-U-C-A | 17 |
| AS strand 5' end | F3 | U-G-A-U-A-A-G-U-A-G-C | 18 |
| AS strand 3' end | F4 | Pho-A-G-U-U-C-A-U-G-C-G-U | 19 |

Note: "Pho" represents 5'-terminus phosphate group; and "-" represents phosphodiester bond.

Synthesis of the nucleotide strands: 20 μL of reaction solution containing various oligonucleotides at a final concentration of 1.6 mM, 50 mM Tris-HCl (pH 8.0), 12 mM MgCl$_2$, 1 mM DTT, 4 mM ATP and 0.005 mg/mL of enzyme was added into a 200 μL microtube, and subjected to incubation respectively at 37° C., 42° C., 45° C. and 50° C. maintained by a PCR thermocycler. 2 h after initiation of the reaction, 1 μL of the reaction solution was sampled and 49 μL of a 10 mM EDTA solution was added to terminate the reaction. Finally, the product was separated using HPLC, and components of each peak were analyzed using mass spectrometry. A proportion of the product was calculated by dividing peak areas of various products in HPLC chromatogram by a total peak area of nucleotides in a whole chromatogram, that is:

$$\text{Product proportion} = \frac{\text{Area(target product or byproduct)}}{\text{Area}(F1 \sim 4 + AS + SS + \text{byproduct})}.$$

Results of the example are listed in Table 12.

TABLE 12

Generation of Products in Ligation Reaction in Example 8

| Variant | Reaction Temperature | Target Product AS + SS (%) | Byproduct | | | | | Total Byproduct |
|---|---|---|---|---|---|---|---|---|
| | | | F2 + F3 | F1 + F3 + F4 | F1 + F2 + F3 | F1 + F2 + F1 | F1 + F2 + F3 + F4 | |
| T4 Rnl2 | 37° C. | 62.4% | 8.0% | 3.2% | 1.7% | 0.6% | 0.1% | 13.6% |
| | 42° C. | 55.6% | 2.5% | 1.9% | 1.7% | 0.2% | 0.1% | 6.4% |

27

TABLE 12-continued

Generation of Products in Ligation Reaction in Example 8

| Variant | Reaction Temperature | Target Product AS + SS (%) | Byproduct | | | | | |
|---|---|---|---|---|---|---|---|---|
| | | | F2 + F3 | F1 + F3 + F4 | F1 + F2 + F3 | F1 + F1 + F2 | F1 + F2 + F3 + F4 | Total By-product |
| | 45° C. | 25.4% | 0.8% | 1.5% | 0.5% | ND | ND | 2.8% |
| | 50° C. | 10.8% | ND | ND | ND | ND | ND | ND |
| Mut3 | 42° C. | 70.2% | 2.0% | 2.0% | 1.5% | 0.1% | ND | 5.6% |
| | 45° C. | 88.9% | 0.8% | 0.1% | 1.0% | ND | ND | 1.9% |
| | 50° C. | 90.2% | ND | ND | ND | ND | ND | ND |
| Mut6 | 42° C. | 75.1% | 1.8% | 1.5% | 1.5% | 0.1% | 0.5% | 5.4% |
| | 45° C. | 88.2% | 0.8% | 1.0% | 0.8% | ND | ND | 2.6% |
| | 50° C. | 90.0% | ND | ND | ND | ND | ND | ND |
| Mut9 | 42° C. | 70.8% | 2.1% | 1.4% | 1.3% | 0.1% | 0.3% | 5.2% |
| | 45° C. | 89.5% | 1.0% | 0.8% | 0.5% | ND | ND | 2.3% |
| | 50° C. | 91.6% | ND | ND | ND | ND | ND | ND |

Note:
"ND" indicates that corresponding product was not detected in liquid phase or mass spectrometry analysis.

In this example, after 2 h of the reaction at 37° C., the yield of the target product of the wild-type T4 Rnl2 was 62.4%, and 13.6% of non-target byproducts were produced, whereas when the reaction temperature was raised to 42° C.', the yield of the target product was slightly decreased, but the byproducts were decreased by about 50%, indicating that raising the reaction temperature can indeed reduce the production of byproducts. When the reaction temperature was further raised to 45° C. and 50° C., the production of byproducts was further reduced. When the reaction temperature was raised to 50° C. no byproduct was produced, but the yield of the target product was only 10.8% at this time because the wild-type T4 Rnl2 was substantially deactivated at high temperatures. Whereas after 2 h of reaction of Mut3, Mut6 and Mut9 at 45° C., the yields of the target product were 88.9%, 88.2% and 89.5%, respectively, and the yields of byproducts were 1.9%, 2.6% and 2.3%, respectively. When Mut3, Mut6 and Mut9 were used to react at 50° C. for 2 h, the yields of the target product were 90.2%, 90.0% and 91.6%, and no byproduct was detected in liquid chromatography-mass spectrometry. The results of this example demonstrate that using the thermostable mutants of the present disclosure to react at high temperatures can significantly reduce the byproducts caused by base mismatching. Moreover, in this example, the yields of the target product of the reaction under high-temperature conditions were significantly higher than that at 37° C., which can be attributed to two factors: on one hand, the enhanced thermal stability of the protein enables sustained activity at high temperatures, and on the other hand, the high-temperature conditions can open some secondary structures that have an adverse effect on the ligation reaction, thereby improving the efficiency of the ligation reaction.

Example 9: T4 Rnl2 Ligase Mutants Ligated Non-Natural Oligonucleotide Strands Containing Modifications at High Temperatures, with Reduced Production of Byproducts Thermostable T4 Rnl2 mutants N193K-R217P-C260D (Mut3), N193K-R217P-S311E-I313V (Mut6), and L168F-N193K-R217P-T303D-S311E-I313V (Mut9) were used in the present example to ligate RNAs comprising non-natural nucleotides at a higher temperature, and the production of byproducts was reduced.

Thermostable T4 Rnl2 mutants N193K-R217P-C260D (Mut3), N193K-R217P-S311E-I313V (Mut6), and L168F-N193K-R217P-T303D-S311E-I313V (Mut9) in Example 4 were used as ligases, and 4 fragments in Table 13 were used as nucleic acid substrates, to synthesize nucleotide strands, with a schematic diagram of the ligation as shown in FIG. 9. As a control experimental group, purified T4 Rnl2 (wild type) was used to react in the control group under the same conditions.

The nucleic acid substrates in this example were all non-natural ribonucleotides, including several common non-natural ribonucleotides in RNA therapeutic design: 2'-methoxy modification (2'-OCH$_3$) at pentose 2'-position, 2'-deoxy-2'-fluoro (2'-F), phosphorothioate modification (P=S) at α-position phosphate, 5'-(E)-vinylphosphonate (5'-VP) at pentose 5'-position, and deoxyribonucleotides incorporated at specific sites. For descriptive convenience, oligonucleotide generated through ligation reaction of F1 and F2 is designated as sense strand (abbreviated as SS, SEQ ID NO: 36), and oligonucleotide generated from F3 and F4 is designated as antisense strand (abbreviated as AS, SEQ ID NO: 37).

TABLE 13

Oligoribonucleotides Used in Ligation Reaction in Example 7

| Fragment | Name | Sequence | SEQ ID NO: |
|---|---|---|---|
| SS strand 5' end | F1 | VP-mA-fC-mG-fC-mA-dT-fG-mA | 20 |
| SS strand 3' end | F2 | Pho-msA-fC-mU-msG-fC-mU-fsA-mC-fU-mU-mA-fU-msC-fA | 21 |
| AS strand 5' end | F3 | mU-fG-mfA-mfU-mA-fA-mG-dU-mA-fG-mC | 22 |
| AS strand 3' end | F4 | Pho-msA-fG-mU-fU-mC-fA-mU-fG-mC-mG-mU | 23 |

Note: "Pho" represents 5'-terminus phosphate group; "-" represents phosphodiester bond; "m" represents 2'-methoxy modification (2'-OCH$_3$); "f" represents 2'-fluoro (2'-F) modification; "s" represents phosphorothioate modification of α-phosphate; "d" represents the nucleotide used being deoxyribonucleotide; and "VP" represents 5'-(E)-vinylphosphonate modification.

Specific synthesis scheme and analysis method of the nucleotide strands were the same as described in Example 8. Results are listed in Table 14.

TABLE 14

Generation of Products in Ligation Reaction in Example 9

| Variant | Reaction Temperature | Target Product AS + SS (%) | Byproduct | | | | | |
| | | | F2 + F3 | F1 + F3 + F4 | F1 + F2 + F3 | F1 + F1 + F2 | F1 + F2 + F3 + F4 | Total By-product |
|---|---|---|---|---|---|---|---|---|
| T4 Rnl2 | 37° C. | 65.4% | 8.5% | 4.1% | 1.5% | 0.6% | 0.2% | 14.9% |
| | 42° C. | 53.3% | 2.0% | 2.0% | 1.5% | 0.1% | 0.2% | 5.8% |
| | 45° C. | 26.5% | 1.0% | 1.2% | 0.3% | ND | ND | 2.5% |
| | 50° C. | 11.0% | ND | ND | ND | ND | ND | ND |
| Mut3 | 42° C. | 72.2% | 1.8% | 1.8% | 1.5% | 0.1% | ND | 5.2% |
| | 45° C. | 89.5% | 0.7% | 0.2% | 0.8% | ND | ND | 1.7% |
| | 50° C. | 89.2% | ND | ND | ND | ND | ND | ND |
| Mut6 | 42° C. | 78.1% | 1.5% | 1.3% | 1.8% | 0.1% | 0.8% | 5.5% |
| | 45° C. | 90.2% | 0.5 | 0.8 | 0.6 | ND | 0.2 | 2.1% |
| | 50° C. | 88.6% | ND | ND | ND | ND | ND | ND |
| Mut9 | 42° C. | 75.6% | 1.2% | 1.3% | 1.6% | 0.2% | 0.4% | 4.7% |
| | 45° C. | 88.2% | 0.5% | 0.5% | 0.9% | ND | 0.1% | 2.0% |
| | 50° C. | 90.1% | ND | ND | ND | ND | ND | ND |

Note:
"ND" indicates that corresponding product was not detected in liquid phase or mass spectrometry analysis.

In this example, after 2 h of the reaction at 37° C., the yield of the target product of the wild-type T4 Rnl2 was 65.4%, and at the same time 14.9% of non-target byproducts were produced, whereas when the reaction temperature was raised to 42° C., the yield of the target product was slightly decreased, but the byproducts were decreased by about 60%. When the reaction temperature was further raised to 45° C. and 50° C., the production of byproducts was further reduced. When the reaction temperature was raised to 50° C., no byproduct production was observed, but the yield of the target product was only 11% at this time because the wild-type T4 Rnl2 was substantially deactivated at high temperatures. Whereas after 2 h of reaction of Mut3, Mut6 and Mut9 at 45° C., the yields of the target product were 89.5%, 90.2% and 88.2%, respectively, and the yields of byproducts were 1.7%, 2.1% and 2.0%, respectively. When Mut3, Mut6 and Mut9 were used to react at 50° C. for 2 h, the yields were 89.2%, 90.2% and 90.1%, and no byproduct was detected in liquid chromatography-mass spectrometry. The results of this example demonstrate that using the thermostable mutants of the present disclosure to react at high temperatures can significantly reduce the byproducts caused by base mismatching, and this effect was not limited to ribonucleotide strands composed of natural ribonucleotides, it was also applicable to ribonucleotide strands composed of non-natural ribonucleotides.

Example 10: Efficiency of Nucleotide Synthesis was Improved by Adding a Procedure of "High-Temperature Denaturation-Low-Temperature Annealing", with Reduced Production of Byproducts 20 µl of reaction solution containing various oligonucleotides (nucleic acid substrates) at a final concentration of 1.6 mM listed in Table 15, 50 mM Tris-HCl (pH 8.0), 12 mM MgCl$_2$, 1 mM DTT, 4 mM ATP and 0.005 mg/ml of wild-type T4 Rnl2 or thermostable ligases L168F-N193K-R217P-T303D-S311E-I313V (Mut9) and A62W-P103G-N166P-L168F-N193K-R217P-T303D-S311E-I313V (Mut23) was added into a 200 µl microtube, and subjected to reaction as shown in FIG. 10, at temperature regulated by a PCR thermocycler.

The present example included several following experimental groups: Experimental Groups 1, 6 and 11, subjected to direct incubation at 37° C. for 4 h; Experimental Groups 2, 7 and 12, subjected to direct incubation at 45° C. for 4 h, Experimental Groups 3, 8 and 13, subjected to direct incubation at 55° C. for 4 h; Experimental Groups 4, 9 and 14, subjected to incubation at 45° C. for 1 h, followed by heating to 55° C. and incubation for 1 h, then cooling to 45° C. for annealing and incubation for 2 h; Experimental Groups 5, 10 and 15, first subjected to incubation at 55° C. for 1 h, followed by cooling to 45° C. for annealing and incubation for 1 h, subsequently heating to 55° C. and incubation for 1 h, and then cooling to 45° C. for annealing and incubation for 1 h. After the reaction was finished, 1 µL of the reaction solution was sampled and 49 µL of a 10 mM EDTA solution was added to terminate the reaction. Reaction products were analyzed by liquid chromatography-mass spectrometry (SS: SEQ ID NO: 38, AS: SEQ ID NO: 39).

TABLE 15

Oligonucleotides Used in Example 10

| Fragment | Name | Sequence | SEQ ID NO: |
|---|---|---|---|
| SS strand 5' end | F1 | VP-mA-mG-mC-mC-msU-fU-mA-mA | 24 |
| SS strand 3' end | F2 | PO4-mA-mU-mA-fC-fA-fA-mU-mA-mU-mU-mA-mA-mG-mC-mG-mA | 25 |
| AS strand 5' end | F3 | mU-mC-mG-mC-mU-fU-msA-msA-msU-mA-mU-mU-mG | 26 |
| AS strand 3' end | F4 | PO,-fU-mA-mU-mU-fU-mA-mA-mG-mG-mC-msU | 27 |

Note: "Pho" represents 5'-terminus phosphate group; "-" represents phosphodiester bond; "m" represents 2'-methoxy modification (2'-OCH$_3$); "f" represents 2'-deoxy-2'-fluoro (2'-F) modification; "s" represents phosphorothioate modification of α-phosphate; "d" represents the nucleotide used being deoxyribonucleotide; and "VP" represents 5'-(E)-vinylphosphonate modification (5'-VP).

The detection and analysis methods were the same as those described in Example 5, and results are listed in Table 16.

TABLE 16

Generation of Products in Ligation Reaction in Example 10

| Variant | Reaction Group | Target Product SS + AS (%) | F2 + F3 (%) | F1+ F2 + F3 (%) | F1+ F2 + F3 + F4 (%) | Total By-product (%) |
|---|---|---|---|---|---|---|
| | | | | | Byproduct | |
| T4 Rnl2 | Experimental Group 1 | 45.2 | 7.6 | 3.0 | 1.5 | 12.1 |
| | Experimental Group 2 | 45.9 | 2.5 | 1.0 | 0.8 | 5.3 |
| | Experimental Group 3 | 6.8 | ND | ND | ND | ND |
| | Experimental Group 4 | 38.0 | 1.8 | 0.8 | 0.4 | 3.0 |
| | Experimental Group 5 | ND | ND | ND | ND | ND |
| Mut9 | Experimental Group 6 | 43.4 | 8.0 | 2.7 | 1.0 | 11.7 |
| | Experimental Group 7 | 68.2 | 2.8 | 1.5 | 0.7 | 5.0 |
| | Experimental Group 8 | 46.8 | ND | ND | ND | ND |
| | Experimental Group 9 | 89.7 | 1.2 | 0.5 | 0.3 | 2.0 |
| | Experimental Group 10 | 91.1 | ND | ND | ND | ND |
| Mut23 | Experimental Group 11 | 50.5 | 8.2 | 2.9 | 1.3 | 12.4 |
| | Experimental Group 12 | 75.5 | 3.0 | 1.8 | 1.0 | 5.8 |
| | Experimental Group 13 | 52.6 | ND | ND | ND | ND |
| | Experimental Group 14 | 92.2 | 1.0 | 0.4 | 0.1 | 1.5 |
| | Experimental Group 15 | 93.5 | ND | ND | ND | ND |

Note:
"ND" indicates that corresponding product was not detected in liquid phase or mass spectrometry analysis.

The results of the example demonstrate that after Mut9 was used to react under a condition of 55° C. for 4 h (Experimental Group 3), the yield of 46.8% was obtained, and no detectable byproduct was produced, while when the wild-type T4 Rnl2 was used to react under the condition of 55° C. for 4 h (Experimental Group 4), no detectable target product was produced. This result demonstrates that Mut9 had better thermal stability and that using Mut9 to react under the condition of 55° C. could effectively reduce the byproduct production. However, according to the results of the example, the byproducts produced after 4 h of reaction of Mut9 under the condition of 55° C. were significantly less than those after 4 h of reaction of Mut9 at 45° C., but the yield of Mut9 after 4 h of reaction under the condition of 55° C. (Experimental Group 8) was 46.8%, lower than 68.2% of Mut9 after 4 h of reaction at 45° C. When Mut9 was first incubated at 45° C. for 1 h, heated to 55° C. and incubated for 1 h, and annealed to 45° C. and incubated for 2 h (Experimental Group 9), the yield of the target product obtained was 89.7%, higher than the yield of 68.2% of Mut9 subjected to direct incubation at 45° C. for 4 h (Experimental Group 7), and the proportion of byproducts was much lower, only 2%. When Mut9 was first incubated at 55° C. for 1 h, then annealed to 45° C. and incubated for 1 h, subsequently heated to 55° C. and incubated for 1 h, and then annealed to 45° C. and incubated for 1 h, the yield obtained was 91.1% (Experimental Group 10), and no byproduct was detected. The experimental result of Mut23 in the present example was substantially consistent with that of Mut9. The above results demonstrate that when the thermostable T4 Rnl2 mutants are used for ligation, adding the step of "high-temperature denaturation-low-temperature annealing" can significantly elevate the yield of the target product while reducing the byproduct production.

Sequence information involved in the present disclosure is partially listed in table below.

| Direction of base sequences is 5'-3' | SEQ ID NO: |
|---|---|
| MFKKYSSLENHYNSKFIEKLYSLGLTGGEWVAREKIHGTNFSLIIERDKVTCAK RTGPILPAEDFFGYEIILKNYADSIKAVQDIMETSAVVSYQVFGEFAGPGIQKNV DYCDKDFYVFDIIVTTESGDVTYVDDYMMESFCNTFKFKMAPLLGRGKFEELI KLPNDLDSVVQDYNFTVDHAGLVDANKCVWNAEAKGEVFTAEGYVLKPCY PSWLRNGNRVAIKCKNSKFSEKKKSDKPIKAKVELSEADNKLVGILACYVTLN RVNNVISKIGEIGPKDFGKVMGLTVQDILEETSREGITLTQADNPSLIKKELVKM VQDVLRPAWIELVS | 1 |
| MFKKYSSLENHYNSKFIEKLYSLGLTGGEWVAREKIHGTNFSLIIERDKVTCAK RTGPILPAEDFFGYEIILKNYADSIKAVQDIMETSAVVSYQVFGEFAGPGIQKNV DYGDKDFYVFDIIVTTESGDVTYVDDYMMESFCNTFKFKMAPLLGRGKFEEL IKLPNDLDSVVQDYNFTVDHAGLVDANKCVWNAEAKGEVFTAEGYVLKPCY PSWLRNGNRVAIKCKNSKFSEKKKSDKPIKAKVELSEADNKLVGILACYVTLN RVNNVISKIGEIGPKDFGKVMGLTVQDILEETSREGITLTQADNPSLIKKELVKM VQDVLRPAWIELVS | 2 |
| ATGTTTAAGAAGTACTCCTCCCTTGAGAACCATTATAACAGCAAGTTCATTG AGAAGCTGTATTCTTTGGGTTTGACGGGCGGTGAATGGGTCGCTCGTGAGA AAATCCACGGCACCAATTTTTCCCTGATCATTGAGCGCGATAAAGTAACGTG CGCGAAGCGCACCGGTCCGATTCTGCCGGCGGAGGATTTCTTCGGCTATGA AATCATTCTCAAAAACTATGCCGACTCCATTAAGGCGGTTCAAGATATCATG GAAACCTCTGCTGTGGTTAGCTACCAGGTTTTCGGCGAGTTTGCGGGACCA GGTATTCAAAAAAACGTGGACTATTGCGACAAGGACTTCTACGTGTTTGAC ATCATCGTTACGACCGAAAGCGGTGATGTTACCTATGTTGACGACTACATGA TGGAGAGCTTCTGCAACACCTTTAAGTTCAAGATGGCACCACTGTTGGGCC | 3 |

-continued

| Direction of base sequences is 5'-3' | SEQ ID NO: |
|---|---|
| GTGGTAAATTTGAAGAGTTGATCAAGCTGCCGAACGATCTGGATTCGGTCG<br>TGCAGGATTACAACTTCACCGTCGACCATGCGGGCCTAGTTGACGCTAATA<br>AATGTGTTTGGAATGCAGAGGCGAAGGGCGAGGTGTTCACCGCAGAGGGC<br>TACGTTCTGAAACCGTGCTACCCGAGCTGGCTGCGTAATGGTAATCGTGTTG<br>CGATTAAGTGCAAGAACAGCAAATTTTCGGAAAAAAAGAAAAGCGATAAA<br>CCGATTAAGGCCAAGGTGGAACTGAGCGAGGCGGATAACAAGTTAGTGGG<br>TATCTTGGCATGTTACGTTACTTTGAATCGCGTTAATAACGTCATCAGCAAAA<br>TCGGTGAAATTGGTCCGAAAGACTTTGGCAAAGTGATGGGTCTGACGGTGC<br>AAGACATCCTGGAGGAAACTTCAAGAGAGGGCATCACCCTGACCCAGGCT<br>GACAACCCGTCTCTGATTAAAAAAGAACTGGTGAAAATGGTGCAGGATGTG<br>TTACGTCCGGCCTGGATTGAACTGGTGAGCTAA | |
| ATGTTTAAGAAGTACTCCTCCCTTGAGAACCATTATAACAGCAAGTTCATTG<br>AGAAGCTGTATTCTTTGGGTTTGACGGGCGGTGAATGGGTCGCTCGTCGAGA<br>AAATCCACGGCACCAATTTTTCCCTGATCATTGAGCGCGATAAAGTAACGTG<br>CGCGAAGCGCACCGGTCCGATTCTGCCGGCGGAGGATTTCTTCGGCTATGA<br>AATCATTCTCAAAAACTATGCCGACTCCATTAAGGCGGTTCAAGATATCATG<br>GAAACCTCTGCTGTGGTTAGCTACCAGGTTTTCGGCGAGTTTGCGGGACCA<br>GGTATTCAAAAAAACGTGGACTATGGTGACAAGGACTTCTACGTGTTTGAC<br>ATCATCGTTACGACCGAAAGCGGTGATGTTACCTATGTTGACGACTACATGA<br>TGGAGAGCTTCTGCAACACCTTTAAGTTCAAGATGGCACCACTGTTGGGCC<br>GTGGTAAATTTGAAGAGTTGATCAAGCTGCCGAACGATCTGGATTCGGTCG<br>TGCAGGATTACAACTTCACCGTCGACCATGCGGGCCTAGTTGACGCTAATA<br>AATGTGTTTGGAATGCAGAGGCGAAGGGCGAGGTGTTCACCGCAGAGGGC<br>TACGTTCTGAAACCGTGCTACCCGAGCTGGCTGCGTAATGGTAATCGTGTTG<br>CGATTAAGTGCAAGAACAGCAAATTTTCGGAAAAAAAGAAAAGCGATAAA<br>CCGATTAAGGCCAAGGTGGAACTGAGCGAGGCGGATAACAAGTTAGTGGG<br>TATCTTGGCATGTTACGTTACTTTGAATCGCGTTAATAACGTCATCAGCAAAA<br>TCGGTGAAATTGGTCCGAAAGACTTTGGCAAAGTGATGGGTCTGACGGTGC<br>AAGACATCCTGGAGGAAACTTCAAGAGAGGGCATCACCCTGACCCAGGCT<br>GACAACCCGTCTCTGATTAAAAAAGAACTGGTGAAAATGGTGCAGGATGTG<br>TTACGTCCGGCCTGGATTGAACTGGTGAGCTAA | 4 |

Sequences as set forth in SEQ ID NOs: 5-23 in the sequence listing are unmodified sequences.

The above-mentioned are merely for preferred embodiments of the present disclosure, but are not intended to limit the present disclosure. For those skilled in the art, various modifications and changes could be made to the present disclosure. Any amendments, equivalent replacements, improvements and so on, made within the spirit and principle of the present disclosure, should be covered within the scope of protection of the present disclosure.

What is claimed is:

1. A T4 RNA ligase 2 mutant, comprising compared with wild-type T4 RNA ligase 2 mutation at any one or more sites of positions 62, 103, 166, 168, 193, 217, 260, 297, 298, 303, 306, 311, 313 and 318 of an amino acid sequence of the wild-type T4 RNA ligase 2, wherein the T4 RNA ligase is at least 85% sequence identity to SEQ ID NO: 1 or 2:

the amino acid sequence of the wild-type T4 RNA ligase 2 is as set forth in SEQ ID NO: 1 or 2; and wherein the T4 RNA ligase 2 is an RNA ligase isolated from T4 bacteriophage.

2. The T4 RNA ligase 2 mutant according to claim 1, wherein the mutation at position 62 comprises A62W;

the mutation at position 103 comprises P103G;

the mutation at position 166 comprises N166P;

the mutation at position 168 comprises L168F;

the mutation at position 193 comprises N193K;

the mutation at position 217 comprises any one of R217A, R217Q, R217N and R217P;

the mutation at position 260 comprises C260D;

the mutation at position 297 comprises T297A;

the mutation at position 298 comprises S298E;

the mutation at position 303 comprises T303D;

the mutation at position 306 comprises any one of Q306A, Q306D and Q306E;

the mutation at position 311 comprises any one of S311E, S311D, S311A and S311V; and the mutation at position 313 comprises I313V.

3. The T4 RNA ligase 2 mutant according to claim 2, wherein the T4 RNA ligase 2 mutant has any one or a combination of following mutation combinations relative to the wild-type T4 RNA ligase 2: N193K-S311D, N193K-R217P, N193K-T303D, N193K-T297A, T297A-Q306D, N193K-I313V, R217P-S298E, R217P-T297A, R217P-I313V, and S311E-I313V.

4. The T4 RNA ligase 2 mutant according to claim 2, wherein the T4 RNA ligase 2 mutant has any one or a combination of following mutation combinations relative to the wild-type T4 RNA ligase 2: R217P-T297A-S311E, R217P-S298E-S311D, R217P-T297A-I313V, N193K-R217P-C260D, R217P-S311E-I313V, R217P-T303D-I313V, N193K-R217P-T303D-S311E, N193K-R217P-

T303D-I313V, N193K-R217P-T303D-V318T, N193K-R217P-S311E-I313V, N193K-R217P-T303D-S311E-I313V, A62W-N193K-R217P-T303D-S311E-I313V, P103G-N193K-R217P-T303D-S311E-I313V, N166P-N193K-R217P-T303D-S311E-I313V, L168F-N193K-R217P-T303D-S311E-I313V and N193K-R217P-C260D-T303D-S311E-I313V-V318T, L168F-N193K-R217P-C260D-S311E-T303D-I313V-V318T, A62W-L168F-N193K-R217P-C260D-T303D-S311E-I313V-V318T, P103G-L168F-N193K-R217P-C260D-T303D-S311E-I313V-V318T, A62W-P103G-L168F-N193K-R217P-C260D-T303D-S311E-I313V-V318T, A62W-P103G-N166P-L168F-N193K-R217P-C260D-T303D-S311E-I313V-V318T, A62W-N166P-L168F-N193K-R217P-C260D-T303D-S311E-I313V-V318T, P103G-N166P-L168F-N193K-R217P-C260D-T303D-S311E-I313V-V318T and N166P-L168F-N193K-R217P-C260D-T303D-S311E-I313V-V318T.

5. The T4 RNA ligase 2 mutant according to claim 2, wherein the T4 RNA ligase 2 mutant has any one or a combination of following mutations relative to the wild-type T4 RNA ligase 2: A62W, P103G, N166P, L168F, R217P, R217A, R217N, R217Q and C260D.

6. The T4 RNA ligase 2 mutant according to claim 4, wherein the T4 RNA ligase 2 mutant has any one of following mutation or combinations relative to the wild-type T4 RNA ligase 2: N193K-R217P-C260D, N193K-R217P-S311E-I313V, N193K-R217P-T303D-S311E-I313V, L168F-N193K-R217P-T303D-S311E-I313V and N193K-R217P-C260D-T303D-S311E-I313V-V318T, L168F-N193K-R217P-C260D-S311E-T303D-I313V-V318T, A62W-L168F-N193K-R217P-C260D-T303D-S311E-I313V-V318T, P103G-L168F-N193K-R217P-C260D-T303D-S311E-I313V-V318T, A62W-P103G-L168F-N193K-R217P-C260D-T303D-S311E-I313V-V318T, A62W-P103G-N166P-L168F-N193K-R217P-C260D-T303D-S311E-I313V-V318T, A62W-N166P-L168F-N193K-R217P-C260D-T303D-S311E-I313V-V318T, P103G-N166P-L168F-N193K-R217P-C260D-T303D-S311E-I313V-V318T and N166P-L168F-N193K-R217P-C260D-T303D-S311E-I313V-V318T.

* * * * *